United States Patent
Herman et al.

(10) Patent No.: US 6,265,171 B1
(45) Date of Patent: *Jul. 24, 2001

(54) METHOD OF DETECTION OF METHYLATED NUCLEIC ACID USING AGENTS WHICH MODIFY UNMETHYLATED CYTOSINE AND DISTINGUISH MODIFIED METHYLATED AND NON-METHYLATED NUCLEIC ACIDS

(75) Inventors: James G. Herman, Lutherville; Stephen B. Baylin, Baltimore, both of MD (US)

(73) Assignee: The Johns Hopkins University School of Medicine, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/490,558

(22) Filed: Jan. 25, 2000

Related U.S. Application Data

(63) Continuation of application No. 08/835,728, filed on Apr. 11, 1997, now Pat. No. 6,017,704, which is a continuation-in-part of application No. 08/656,716, filed on Jun. 3, 1996, now Pat. No. 5,786,146.

(51) Int. Cl.[7] ............................. C12Q 1/68; C12P 19/34
(52) U.S. Cl. ............................................. 435/6; 435/91.2
(58) Field of Search ........................................ 435/6, 91.2

(56) References Cited

U.S. PATENT DOCUMENTS

| | | |
|---|---|---|
| 5,324,634 | 6/1994 | Zucker . |
| 5,595,885 | 1/1997 | Stetler-Stevenson et al. . |

OTHER PUBLICATIONS

Herman et al., Proc. Natl. Acad. Sci. USA 93, 9821–9826 (Sep. 1996).*
De Clerck et al., Gene 139, 185–191 (1994).*
Hammani et al., J. Biol. Chem. 271(41), 25498–25505 (Oct. 1996).*
Kawaguchi et al., Arch. Dermatol. Res. 288(1), 39–44 (1996)(abstract only).*
Clark, et al., High sensitivity mapping of methylated cytosines, *Nucleic Acids Research,* 22(15):2990, 1994.
Frommer, et al., A genomic sequencing protocol that yields a positive display of 5–methylcytosine residues in individual DNA strands, *Proc. Natl. Acad. Sci. USA,* 89:1827, Mar. 1992.
Graff, et al., E–Cadherin Expression is Silenced by DNA Hypermethylation in Human Breast and Prostate Carcinomas, *Cancer Research,* 55:5195, Nov. 15, 1995.
Herman, et al., MSP: A Novel PCR Assay for Methylation Status of CpG Islands, *Biological Sciences:Medical Sciences,* pp. 1–12.
Herman, et al., Inactivation of the CDKN2/p16/MTS1 Gene is Frequently Associated with Aberrant DNA Methylation in All Common Human Cancers, *Cancer Research,* 55:4525, Oct. 15, 1995.
Lowe, et al., A computer program for selection of oligonucleotide primers for polymerase chain reactions, *Nucleic Acids research,* 18(7):1757, Mar. 2, 1990.
Myohanene, et al., Automated fluorescent genomic sequencing as applied to the methylation analysis of the human orthine decarboxylase gene, *DNA Sequence–The Journal of Sequencing and Mapping,* 5:1, 1994.
Park, et al., CpG island Promoter region Methylation Patterns of the Inactive–X–Chromosome Hypoxanthine Phosporibosyltransferase (Hprt) Gene, *Molecular and Cellular Biology,* 14(12):7975, Dec. 1994.
Raizis, et al., A Bisulfite Method of 5–Methylcytosine Mapping That Minimizes Template Degradation, *Analytical Biochemistry,* 226:161, 1995.
Reeben, et al., Sequencing of the rat light neurofilament promoter reveals difference in ethylation between expressing and non–expressing cell lines, but not tissues, *Gene,* 157:325, 1995.
Tasheva and Roufa, Deoxycytidine Methylation and the Origin of Spontaneous transition Mutations in Mammalian Cells, *Samatic Cell and Molecular genetics,* 19(3):275, 1993.
Gonzales–Zulueta et al., Methylation of the 5' CpG Island of the p16/CDKN2 Tumor Suppressor Gene in Normal and Transformed Human Tissues Correlates with Gene Silencing, *Cancer Research,* 55:4531–4535.
Zuccotti et al., Polymerase Chain Reaction for the Detection of Methylation of a Specific CpG Site in the C6pd Gene of Mouse Embryos, *Methods in Enzymology* 225:557–567.
Stetler–Stevenson et al., "Tissue Inhibitor of Metalloproteinases–2 (TIMP–2) mRNA Expression in Tumor Cell Lines and Human Tumor Tissues," *J. Biol. Chem.* Aug. 15, 1990, vol. 265, No. 23, pp. 13933–13938.
Frommer et al., "A genomic sequencing protocol that yields a positive display of 5–methylcyltosine residues in individual DNA strands," *Proc. Natl. Acad. Sci. USA,* Mar. 1992, vol. 89, pp. 1827–1831.

* cited by examiner

*Primary Examiner*—Kenneth R. Horlick
(74) *Attorney, Agent, or Firm*—Gray Cary Ware & Freidenrich LLP; Lisa A. Haile

(57) ABSTRACT

The present invention provides a method for detecting a methylated CpG-containing nucleic acid present in a specimen by contacting the specimen with an agent that modifies unmethylated cytosine and amplifying the CpG-containing nucleic acid using CpG-specific oligonucleotide primers. The present invention provides an improved method of methylation detection by facilitating the rapid identification of DNA methylation patterns in a CpG-containing nucleic acid.

14 Claims, 3 Drawing Sheets

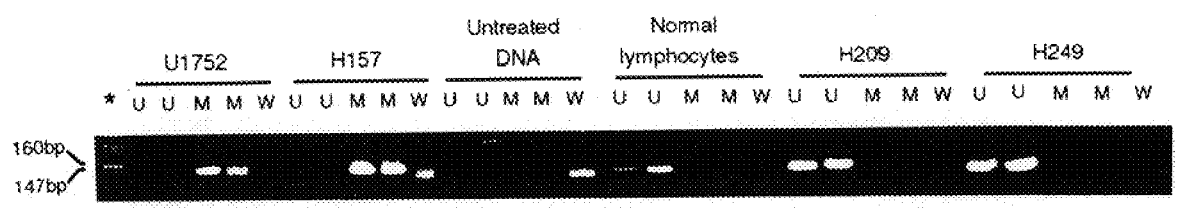
FIG. 2A
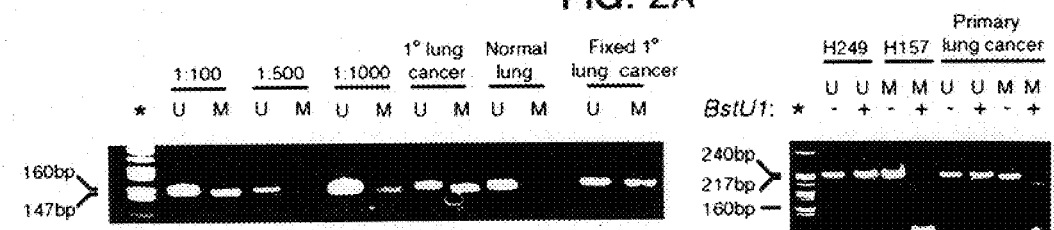
FIG. 2B
FIG. 2D
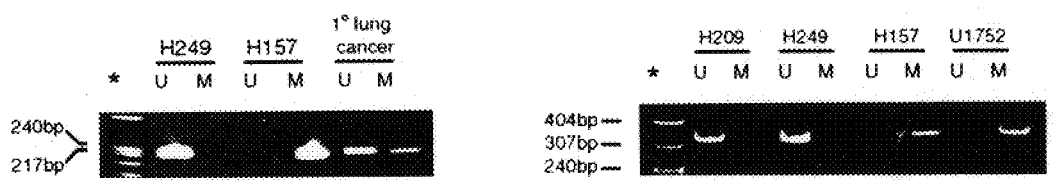
FIG. 2C
FIG. 2E

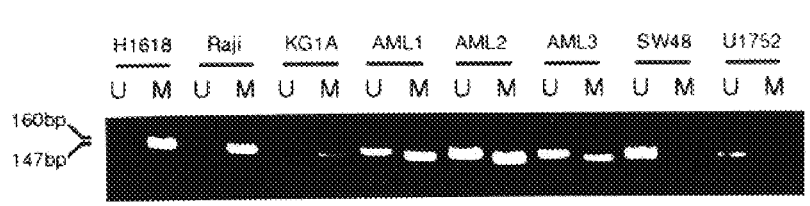
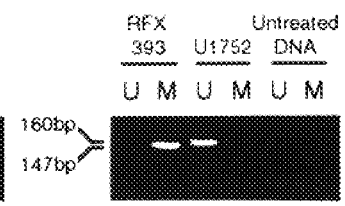
FIG. 3A
FIG. 3C
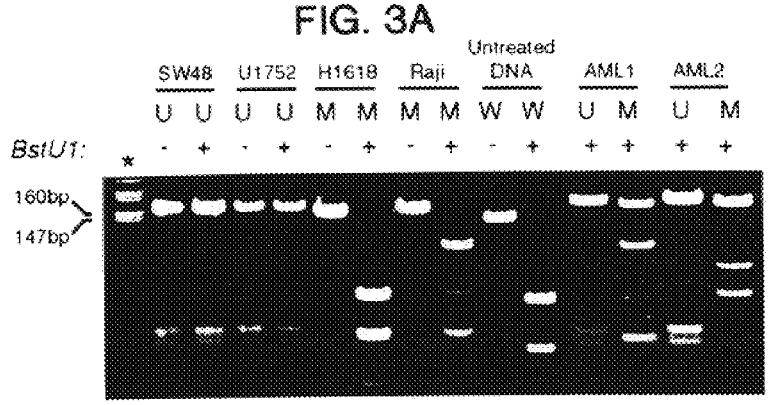
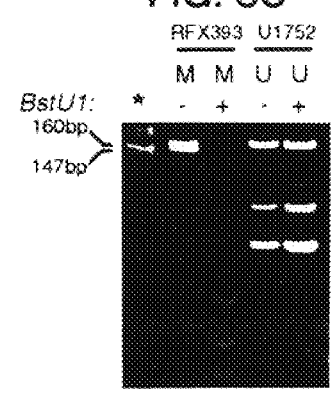
FIG. 3B
FIG. 3D
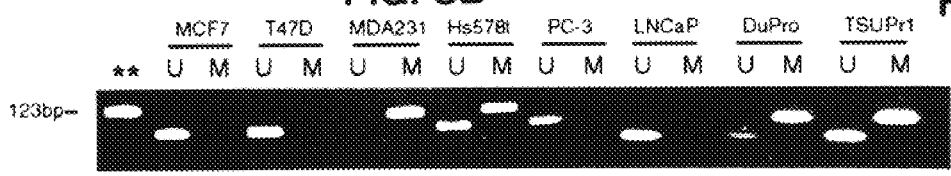
FIG. 3E

US 6,265,171 B1

METHOD OF DETECTION OF METHYLATED NUCLEIC ACID USING AGENTS WHICH MODIFY UNMETHYLATED CYTOSINE AND DISTINGUISH MODIFIED METHYLATED AND NON-METHYLATED NUCLEIC ACIDS

This application is a continuation of U.S. application Ser. No. 08/835,728, filed Apr. 11, 1997, issued on Jan. 25, 2000 as U.S. Pat. No. 6,017,704; which is a continuation-in-part of U.S. application Ser. No. 08/656,716, filed Jun. 3, 1996, issued on Jul. 28, 1998 as U.S. Pat. No. 5,786,146; the entire contents of which are hereby incorporated herein by reference.

FIELD OF THE INVENTION

The present invention relates generally to regulation of gene expression, and more specifically to a method of determining the DNA methylation status of CpG sites in a given locus.

BACKGROUND OF THE INVENTION

In higher order eukaryotes DNA is methylated only at cytosines located 5' to guanosine in the CpG dinucleotide. This modification has important regulatory effects on gene expression, especially when involving CpG rich areas, known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosome of females. Abberant methylation of normally unmethylated CpG islands has been described as a frequent event in immortalized and transformed cells, and has been associated with transcriptional inactivation of defined tumor suppressor genes in human cancers.

Human cancer cells typically contain somatically altered genomes, characterized by mutation, amplification, or deletion of critical genes. In addition, the DNA template from human cancer cells often displays somatic changes in DNA methylation (E. R. Fearon, et al., *Cell*, 61:759, 1990; P. A. Jones, et al., *Cancer Res.*, 46:461, 1986; R. Holliday, *Science*, 238:163, 1987; A. De Bustros, et al., *Proc. Natl. Acad. Sci., USA*, 85:5693, 1988); P. A. Jones, et al., *Adv. Cancer Res.*, 54:1, 1990; S. B. Baylin, et al., *Cancer Cells*, 3:383, 1991; M. Makos, et al., *Proc. Natl. Acad Sci., USA*, 89:1929, 1992; N. Ohtani-Fujita, et al., *Oncogene*, 8:1063, 1993). However, the precise role of abnormal DNA methylation in human tumorigenesis has not been established. DNA methylases transfer methyl groups from the universal methyl donor S-adenosyl methionine to specific sites on the DNA. Several biological functions have been attributed to the methylated bases in DNA. The most established biological function is the protection of the DNA from digestion by cognate restriction enzymes. The restriction modification phenomenon has, so far, been observed only in bacteria. Mammalian cells, however, possess a different methylase that exclusively methylates cytosine residues on the DNA, that are 5' neighbors of guanine (CpG). This methylation has been shown by several lines of evidence to play a role in gene activity, cell differentiation, tumorigenesis, X-chromosome inactivation, genomic imprinting and other major biological processes (Razin, A., H., and Riggs, R. D. eds. in DNA Methylation Biochemistry and Biological Significance, Springer-Verlag, New York, 1984).

A CpG rich region, or "CpG island", has recently been identified at 17p13.3, which is aberrantly hypermethylated in multiple common types of human cancers (Makos, M., et al., *Proc. Natl. Acad. Sci. USA*, 89:1929, 1992; Makos, M., et al., *Cancer Res.*, 53:2715, 1993; Makos, M., et al., *Cancer Res.* 53:2719, 1993). This hypermethylation coincides with timing and frequency of 17p losses and p53 mutations in brain, colon, and renal cancers. Silenced gene transcription associated with hypermethylation of the normally unmethylated promoter region CpG islands has been implicated as an alternative mechanism to mutations of coding regions for inactivation of tumor suppressor genes (Baylin, S. B., et al., *Cancer Cells*, 3:383, 1991; Jones, P. A. and Buckley, J. D., *Adv. Cancer Res.*, 54:1–23, 1990). This change has now been associated with the loss of expression of VHL, a renal cancer tumor suppressor gene on 3p (J. G. Herman, et al., *Proc. Natl. Acad. Sci. USA*, 91:9700–9704, 1994), the estrogen receptor gene on 6q (Ottaviano, Y. L., et al., *Cancer Res.*, 54:2552, 1994) and the H19 gene on 11p (Steernan, M. J. C., et al., *Nature Genetics*, 7:433, 1994).

In eukaryotic cells, methylation of cytosine residues that are immediately 5' to a guanosine, occurs predominantly in CG poor regions (Bird, A., *Nature*, 321:209, 1986). In contrast, discrete regions of CG dinucleotides called CpG islands remain unmethylated in normal cells, except during X-chromosome inactivation (Migeon, et al., supra) and parental specific imprinting (Li, et al., *Nature*, 366:362, 1993) where methylation of 5' regulatory regions can lead to transcriptional repression. De novo methylation of the Rb gene has been demonstrated in a small fraction of retinoblastomas (Sakai, et al, *Am. J. Hum. Genet.*, 48:880, 1991), and recently, a more detailed analysis of the VHL gene showed aberrant methylation in a subset of sporadic renal cell carcinomas (Herman, et al., *Proc. Natl. Acad. Sci., U.S.A.*, 91:9700, 1994). Expression of a tumor suppressor gene can also be abolished by de novo DNA methylation of a normally unmethylated 5' CpG island (Issa, et al., *Nature Genet.*, 7:536, 1994; Herman, et al., supra; Merlo, et al., *Nature Med.*, 1:686, 1995; Herman, et al., *Cancer Res.*, 56:722, 1996; Graff, et al., *Cancer Res.*, 55:5195, 1995; Herman, et al., *Cancer Res.*, 55:4525, 1995).

Most of the methods developed to date for detection of methylated cytosine depend upon cleavage of the phosphodiester bond alongside cytosine residues, using either methylation-sensitive restriction enzymes or reactive chemicals such as hydrazine which differentiate between cytosine and its 5-methyl derivative. The use of methylation-sensitive enzymes suffers from the disadvantage that it is not of general applicability, since only a limited proportion of potentially methylated sites in the genome can be analyzed. Genomic sequencing protocols which identify a 5-MeC residue in genomic DNA as a site that is not cleaved by any of the Maxam Gilbert sequencing reactions, are a substantial improvement on the original genomic sequencing method, but still suffer disadvantages such as the requirement for large amount of genomic DNA and the difficulty in detecting a gap in a sequencing ladder which may contain bands of varying intensity.

Mapping of methylated regions in DNA has relied primarily on Southern hybridization approaches, based on the inability of methylation-sensitive restriction enzymes to cleave sequences which contain one or more methylated CpG sites. This method provides an assessment of the overall methylation status of CpG islands, including some quantitative analysis, but is relatively insensitive, requires large amounts of high molecular weight DNA and can only provide information about those CpG sites found within sequences recognized by methylation-sensitive restriction enzymes. A more sensitive method of detecting methylation patterns combines the use of methylation-sensitive enzymes and the polymerase chain reaction (PCR). After digestion of DNA with the enzyme, PCR will amplify from primers flanking the restriction site only if DNA cleavage was prevented by methylation. Like Southern-based approaches, this method can only monitor CpG methylation in methylation-sensitive restriction sites. Moreover, the restriction of unmethylated DNA must be complete, since any uncleaved DNA will be amplified by PCR yielding a false positive result for methylation. This approach has been useful in studying samples where a high percentage of alleles of interest are methylated, such as the study of imprinted genes and X-chromosome inactivated genes. However, difficulties in distinguishing between incomplete restriction and low numbers of methylated alleles make this approach unreliable for detection of tumor suppressor gene hypermethylation in small samples where methylated alleles represent a small fraction of the population.

Another method that avoids the use of restriction endonucleases utilizes bisulfite treatment of DNA to convert all unmethylated cytosines to uracil. The altered DNA is amplified and sequenced to show the methylation status of all CpG sites. However, this method is technically difficult, labor intensive and without cloning amplified products, it is less sensitive than Southern analysis, requiring approximately 10% of the alleles to be methylated for detection.

Identification of the earliest genetic changes in tumorigenesis is a major focus in molecular cancer research. Diagnostic approaches based on identification of these changes are likely to allow implementation of early detection strategies and novel therapeutic approaches targeting these early changes might lead to more effective cancer treatment.

SUMMARY OF THE INVENTION

The precise mapping of DNA methylation patterns in CpG islands has become essential for understanding diverse biological processes such as the regulation of imprinted genes, X-chromosome inactivation, and tumor suppressor gene silencing in human cancer. The present invention provides a method for rapid assessment of the methylation status of any group of CpG sites within a CpG island, independent of the use of methylation-sensitive restriction enzymes. Despite the knowledge of those of skill in the art regarding the use of PCR and the use of bisulfite modification, independently, until the present invention, no one had prepared primers that were specific for the bisulfite reaction such that the PCR reaction itself was used to distinguish between the chemically modified methylated and unmethylated DNA.

The method of the invention includes modification of DNA by sodium bisulfite or a comparable agent which converts all unmethylated but not methylated cytosines to uracil, and subsequent amplification with primers specific for methylated versus unmethylated DNA. This method of "methylation specific PCR" or MSP, requires only small amounts of DNA, is sensitive to 0.1% of methylated alleles of a given CpG island locus, and can be performed on DNA extracted from paraffin-embedded samples, for example. MSP eliminates the false positive results inherent to previous PCR-based approaches which relied on differential restriction enzyme cleavage to distinguish methylated from unmethylated DNA.

In a particular aspect of the invention, MSP is useful for identifying promoter region hypermethylation changes associated with transcriptional inactivation in tumor suppressor genes, for example, p16, p15, E-cadherin and VHL, in human neoplasia. Other genes that are shown to be methylated include the estrogen receptor, MDGI, GST-pi, calcitonin, HIC-1, endothelin B receptor, TIMP-2, 06-MGMT, MLH1, MSH2, and GFAP. Of those, the estrogen receptor, MDGI, GST-pi, calcitonin, HIC-1, endothelin B receptor, TIMP-2, 06-MGMT, and MLH1 were shown by MSP to be hypennethylated in neoplastic tissue as compared with normal tissue. For the first time, the invention provides evidence that TIMP-2, a tissue inhibitor of metalloproteinases, is hypermethylated in neoplastic tissue as compared with normal tissue.

BRIEF DESCRIPTION OF THE DRAWINGS

FIGS. 2A–2E show polyacrylamide gels with the Methylation Specific PCR products of p16. Primer sets used for amplification are designated as unmethylated (U), methylated (M), or unmodified/wild-type (W).* designates the molecular weight marker pBR322-MspI digest. Panel A shows amplification of bisulfite-treated DNA from cancer cell lines and normal lymphocytes, and untreated DNA (from cell line H249). Panel B shows mixing of various amount of H157 DNA with 1 µg of H249 DNA prior to bisulfite treatment to assess the detection sensitivity of MSP for methylated alleles. Modified DNA from a primary lung cancer sample and normal lung are also shown. Panel C shows amplification with the p16-U2(U) primers, and p16-M2(M) described in Table 1. Panel D shows the amplified p16 products of panel C restricted with BstUI(+) or not restricted (−). Panel E shows results of testing for regional methylation of CpG islands with MSP, using sense primers p16-U2(U) and p16-M2(M), which are methylation specific, and an antisense primer which is not methylation specific.

FIGS. 3A–3E show polyacrylamide gels of MSP products from analysis of several genes. Primer sets used for amplification are not designated as unmnethylated (U), methylated (M), or unmodified/wild-type (W). * designates the molecular weight marker pBR322-MspI digest and ** designates the 123 bp molecular weight marker. All DNA samples were bisulfite treated except those designated untreated. Panel A shows the results from MSP for p15. Panel B shows the p15 products restricted with BstUI(+) or not restricted (−). Panel C shows the products of MSP for VHL. Panel D shows the VHL products restricted with BstUI(+) or not restricted (−). Panel E shows the products of MSP for E-cadherin.

DESCRIPTION OF THE PREFERRED EMBODIMENTS

Figure 1:
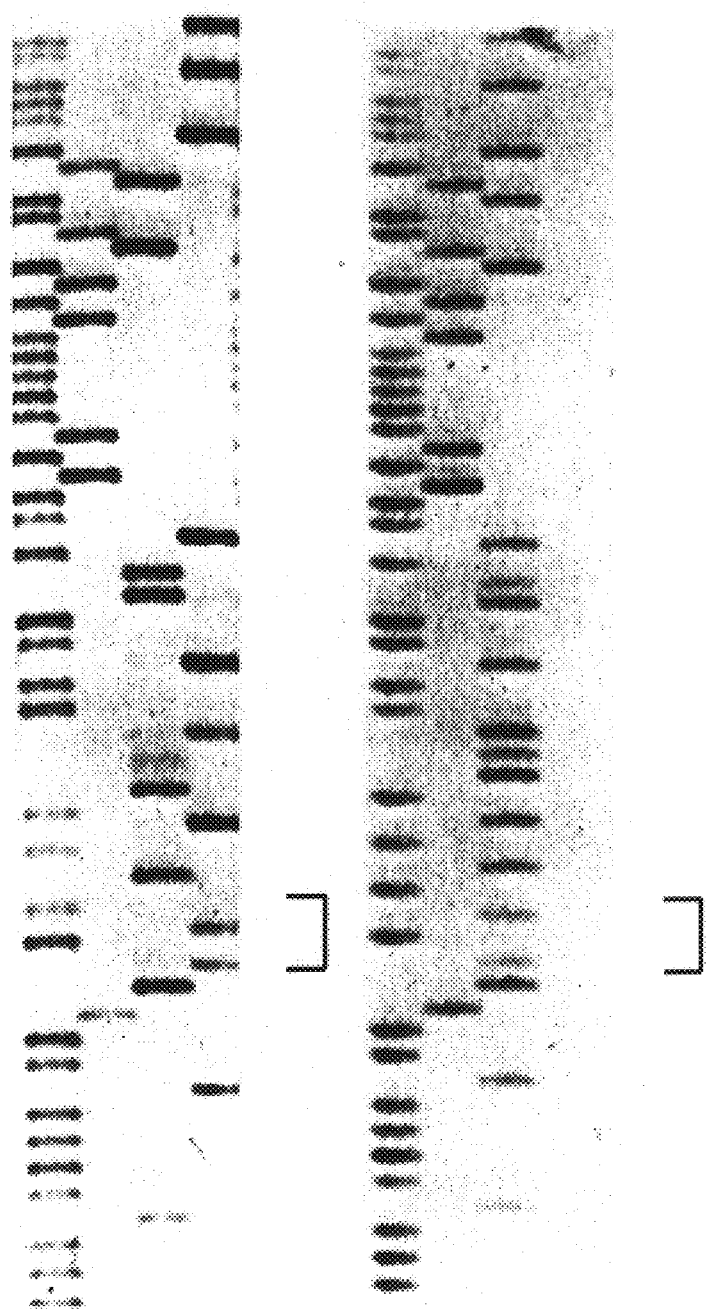
FIG. 1 shows genomic sequencing of p16. The sequence shown has the most 5' region at the bottom of the gel, beginning at +175 in relation to a major transcriptional start site (Hara, et al., *Mol. Cell Biol.*, 16:859, 1996). All cytosines in the unmethylated cell line H249 have been converted to thymidine, while all C's in CpG dinucleotides in the methylated cell H157 remains as C, indicating methylation.] enclosed a BstUI site which is at −59 in relation to the transnational start site in Genbank sequence U12818 (Hussussian, et al., *Nat. Genet.*, 8:15, 1994), but which is incorrectly identified as CGCA in sequence X94154 (Hara, et al., supra). This CGCG site represents the 3' location of the sense primer used for p16 MSP.

The present invention provides methylation specific PCR (MSP) for identification of DNA methylation patterns. MSP uses the PCR reaction itself to distinguish between modified methylated and unmethylated DNA, which adds an improved sensitivity of methylation detection.

Unlike previous genomic sequencing methods for methylation identification which utilizes amplification primers which are specifically designed to avoid the CpG sequences, MSP primers themselves are specifically designed to recognize CpG sites to take advantage of the differences in methylation to amplify specific products to be identified by the invention assay.

As illustrated in the Examples below, MSP provides significant advantages over previous PCR and other methods used for assaying methylation. MSP is markedly more sensitive than Southern analyses, facilitating detection of low numbers of methylated alleles and the study of DNA from small samples. MSP allows the study of paraffin-embedded materials, which could not previously be analyzed by Southern analysis. MSP also allows examination of all CpG sites, not just those within sequences recognized by methylation-sensitive restriction enzymes. This markedly increases the number of such sites which can be assessed and will allow rapid, fine mapping of methylation patterns throughout CpG rich regions. MSP also eliminates the frequent false positive results due to partial digestion of methylation-sensitive enzymes inherent in previous PCR methods for detecting methylation. Furthermore, with MSP, simultaneous detection of unmethylated and methylated products in a single sample confirms the integrity of DNA as a template for PCR and allows a semi-quantitative assessment of allele types which correlates with results of Southern analysis. Finally, the ability to validate the amplified product by differential restriction patterns is an additional advantage.

The only technique that can provide more direct analysis than MSP for most CpG sites within a defined region is genomic sequencing. However, MSP can provide similar information and has the following advantages. First, MSP is much simpler and requires less than genomic sequencing, with a typical PCR and gel analysis taking 4–6 hours. In contrast, genomic sequencing, amplification, cloning, and subsequent sequencing may take days. MSP also avoids the use of expensive sequencing reagents and the use of radioactivity. Both of these factors make MSP better suited for the analysis of large numbers of samples. Third, the use of PCR as the step to distinguish methylated from unmethylated DNA in MSP allows for significant increase in the sensitivity of methylation detection. For example, if cloning is not used prior to genomic sequencing of the DNA, less than 10% methylated DNA in a background of unmethylated DNA cannot be seen (Myohanen, et al., supra). The use of PCR and cloning does allow sensitive detection of methylation patterns in very small amounts of DNA by genomic sequencing (Frommer, et al., *Proc. Natl. Acad. Sci. USA*, 89:1827, 1992; Clark, et al., *Nucleic Acids Research*, 22:2990, 1994). However, this means in practice that it would require sequencing analysis of 10 clones to detect 10% methylation, 100 clones to detect 1% methylation, and to reach the level of sensitivity we have demonstrated with MSP (1:1000), one would have to sequence 1000 individual clones.

In a first embodiment, the invention provides a method for detecting a methylated CpG-containing nucleic acid, the method including contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. It is understood that while the amplification step is optional, it is desirable in the preferred method of the invention. The method of the invention relies on the PCR reaction itself to distinguish between modified (e.g., chemically modified) methylated and unmethylated DNA.

The term "modifies" as used herein means the conversion of an unmethylated cytosine to another nucleotide which will distinguish the unmethylated from the methylated cytosine. Preferably, the agent modifies unmethylated cytosine to uracil. Preferably, the agent used for modifying unmethylated cytosine is sodium bisulfite, however, other agents that similarly modify unmethylated cytosine, but not methylated cytosine can also be used in the method of the invention. Sodiun bisulfite ($NaHSO_3$) reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA.

The primers used in the invention for amplification of the CpG-containing nucleic acid in the specimen, after bisulfite modification, specifically distinguish between untreated or unmodified DNA, methylated, and non-methylated DNA. MSP primers for the non-methylated DNA preferably have a T in the 3' CG pair to distinguish it from the C retained in methylated DNA, and the compliment is designed for the antisense primer. MSP primers usually contain relatively few Cs or Gs in the sequence since the Cs will be absent in the sense primer and the Gs absent in the antisense primer (C becomes modified to U(uracil) which is amplified as T(thymidine) in the amplification product).

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with the 5' and 3' flanking sequences to hybridize therewith and permit amplification of the genomic locus. While exemplary primers are provided in SEQ ID NO: 105–208, it is understood that any primer that hybridizes with the target sequences in SEQ ID NO: 1–104 is included in the invention and is useful in the method of the invention for detecting methylated nucleic acid, as described.

Oligonucleotide primers of the invention are employed in the amplification process which is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing specimen used for detection of methylated CpG may be from any source including brain, colon, urogenital, hematopoietic, thymus, testis, ovarian, uterine, prostate, breast, colon, lung and renal tissue and may be extracted by a variety of techniques such as that described by Maniatis, et al. (*Molecular Cloning: A Laboratory Manual*, Cold Spring Harbor, N.Y., pp 280, 281, 1982).

If the extracted sample is impure (e.g., plasma, serum, stool, ejaculate, sputum, saliva, cerebrospinal fluid or blood or a sample embedded in parrafin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffinann-Berling (CSH-Quantitative Biology, 43:63, 1978) and techniques for using RecA are reviewed in C. Radding (*Ann. Rev. Genetics*, 16:405–437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated lona-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E.coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Preferably, the method of amplifying is by PCR, as described herein and as is commonly used by those of ordinary skill in the art. Alternative methods of amplification have been described and can also be employed as long as the methylated and non-methylated loci amplified by PCR using the primers of the invention is similarly amplified by the alternative means.

The amplified products are preferably identified as methylated or non-methylated by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Optionally, the methylation pattern of the nucleic acid can be confirmed by restriction enzyme digestion and Southern blot analysis. Examples of methylation sensitive restriction endonucleases which can be used to detect 5'CpG methylation include SmaI, SacII, EagI, MspI, HpaII, BstUI and BssHII, for example.

The invention provides a method for detecting a cell having a methylated CpG island or a cell proliferative disorder associated with methylated CpG in a tissue or biological fluid of a subject, comprising contacting a target cellular component suspected of expressing a gene having a methylated CpG or having a CpG-associated disorder, with an agent which binds to the component. The target cell component can be nucleic acid, such as DNA or RNA, or protein. When the component is nucleic acid, the reagent is a nucleic acid probe or PCR primer. When the cell component is protein, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody, or will be able to ascertain such, using routine experimentation.

Actively transcribed genes generally contain fewer methylated CGs than the average number in DNA. Hypermethylation can be detected by restriction endonuclease treatment and Southern blot analysis. Therefore, in a method of the invention, when the cellular component detected is DNA, restriction endonuclease analysis is preferable to detect hypermethylation of the promoter for example. Any restriction endonuclease that includes CG as part of its recognition site and that is inhibited when the C is methylated, can be utilized. Preferably, the methylation sensitive restriction endonuclease is BssHII, MspI, or HpaII, used alone or in combination. Other methylation sensitive restriction endonucleases will be known to those of skill in the art.

For purposes of the invention, an antibody or nucleic acid probe specific for a gene or gene product may be used to detect the presence of methylation either by detecting the level of polypeptide (using antibody) or methylation of the polynucleotide (using nucleic acid probe) in biological fluids or tissues. For antibody based detection, the level of the polypeptide is compared with the level of polypeptide found in a corresponding "normal" tissue. Oligonucleotide primers based on any coding sequence region of the promoter in the TIMP-2, estrogen receptor, GST-pi, calcitonin, HIC-1 or MLH1 sequence, for example, are useful for amplifying DNA, for example by PCR. These genes are merely listed as examples and are not meant to be limiting. Any specimen containing a detectable amount of polynucleotide or antigen can be used. Preferably the subject is human.

The present invention provides the finding that TIMP-2 is methylated in cancer tissue as compared to normal tissue. For example, TIMP-2 was found to be methylated in colon cancer tissue but not in normal colon tissue. The method for detecting a cell expressing a gene such as TIMP-2, or a cell proliferative disorder associated with methylation of CpG containing TIMP-2, or any gene including those described above, can be utilized for detection of residual cancer or other malignancies in a subject in a state of clinical remission. Additionally, the method for detecting polypeptide in cells is useful for detecting a cell proliferative disorder by measuring the level of polypeptide in cells expressing the polypeptide, in a suspect tissue in comparison with the polypeptide expressed in normal cells or tissue. Using the method of the invention, expression of any gene, such as TIMP-2, can be identified in a cell and the appropriate course of treatment can be employed (e.g., sense gene therapy or drug therapy). The expression pattern of the gene, e.g., TIMP-2, may vary with the stage of malignancy of a cell, therefore, a sample such as breast or colon tissue can be screened with a panel of gene or gene product specific reagents (i.e., nucleic acid probes or antibodies) to detect gene expression, e.g., TIMP-2, and diagnose the stage of malignancy of the cell.

Monoclonal antibodies can be used in the method of the invention, for example, in immunoassays in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such inimunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of TIMP-2. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, TIMP-2 may be detected by the monoclonal antibodies when present in biological fluids and tissues. Any sample containing a detectable amount of TIMP-2 can be used. A sample can be a liquid such as ejaculate, urine, saliva, cerebrospinal fluid, blood, serum and the like, or a solid or semi-solid such as tissues, feces, and the like, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-TIMP-2 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

In using a monoclonal antibody for the in vivo detection of antigen, the detectably labeled monoclona I antibody is given in a dose which is diagnostically effective. The term "diagnostically effective" means that the amount of detectably labeled monoclonal antibody is administered in sufficient quantity to enable detection of the site having the TIMP-2 antigen for which the monoclonal antibodies are specific.

The concentration of detectably labeled monoclonal antibody which is administered should be sufficient such that the binding to those cells having TIMP-2 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dry, $^{52}$Cr, and $^{56}$Fe.

Monoclonal antibodies used in the method of the invention can be used to monitor the course of amelioration of TIMP-2 associated cell proliferative disorder. Thus, by measuring the increase or decrease in the number of cells expressing TIMP-2 or changes in TIMP-2 present in various body fluids, it would be possible to determine whether a particular therapeutic regiment aimed at ameliorating the disorder is effective.

The term "modulate" envisions the suppression of methylation of TIMP-2 (e.g., promoter) or augmentation of TIMP-2 gene expression when TIMP-2 is under-expressed. When a cell proliferative disorder is associated with TIMP-2 expression, such methylation suppressive reagents as 5-azacytadine can be introduced to a cell. Alternatively, when a cell proliferative disorder is associated with under-expression of TIMP-2 polypeptide, a sense polynucleotide sequence (the DNA coding strand) encoding the promoter region or the promoter operably linked to the structural gene, or TIMP-2 polypeptide can be introduced into the cell.

The present invention also provides gene therapy for the treatment of cell proliferative disorders which are mediated by TIMP-2. Such therapy would achieve its therapeutic effect by introduction of the appropriate TIMP-2 polynucleotide which contains either a normal TIMP-2 promoter region alone or in combination with a TIMP-2 structural gene (sense), into cells of subjects having the proliferative disorder. Alternatively, the TIMP-2 structural gene could be introduced operably linked to a heterologous promoter. Delivery of sense TIMP-2 promoter polynucleotide constructs can be achieved using a recombinant expression vector such as a chimeric virus or a colloidal dispersion system.

The promoter polynucleotide sequences used in the method of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense promoter for TIMP-2 or a sense promoter operably linked with the structural gene for the corresponding gene (e.g., TIMP-2 promoter with TIMP-2 structural gene).

The invention also relates to a medicament or pharmaceutical composition comprising a TIMP-2 promoter polynucleotide or a TIMP-2 promoter polynucleotide operably linked to the TIMP-2 structural gene, respectively, in a pharmaceutically acceptable excipient or medium wherein the medicament is used for therapy of TIMP-2 associated cell proliferative disorders.

The invention also provides the use of MSP for in situ methylation analysis. For example, MSP can be used to detect methylation of DNA in the nucleus of an intact cell. A tissue section, a cell or population of cells is placed or immobilized on a solid support (e.g., a slide) and MSP primers used directly on the cell for amplification of the appropriate sequences. The primers are typically detectably labeled with a reporter means, e.g., fluorescent label. Alternatively, a probe that detects or hybridizes with the MSP amplified sequences is used to detect amplification of methylated sequences. In situ methylation analysis using MSP is useful, for example, in detecting nucleic acid having a mutant nucleotide sequence associated with a primary tumor in the adjacent histopathologic surgical margins and more distant tissues, such as regional lymph nodes, which are apparently "normal" when examined by standard histological techniques. Using MSP, it is possible to detect target nucleic acids from cells previously associated with a large number of disease states which are present in tissue that appears normal. MSP in situ can be used as an adjunct to cytopathology, to screen high-risk populations and to monitor high risk patients undergoing chemoprevention or chemotherapy.

Exemplary target polynucleotide sequences to which the primer of the invention hybridizes have a sequence as listed below.

|  |  | SEQ ID NO |
|---|---|---|
| Wild type p16 | 5'-GCGGTCCGCCCCACCCTCTG-3'; | 1 |
|  | 5'-CCACGGCCGCGGCCCG-3'; | 2 |
| Methylated p16-1* | 5'-GCGATCCGCCCCACCCTCTAATAA-3'; | 3 |
|  | 5'-TTACGGTCGCGGTTCGGGGTC-3'; | 4 |
| Unmethylated p16-1 | 5'-ACAATCCACCCCACCCTCTAATAA-3'; | 5 |
|  | 5'-TTATGGTTGTGGTTTGGGGTTG-3'; | 6 |
| Methylated p16-2 | 5'-GCGATCCGCCCCACCCTCTAATAA-3'; | 7 |
|  | 5'-CGGTCGGAGGTCGATTTAGGTGG-3'; | 8 |
| Unmethylated p16-2 | 5'-ACAATCCACCCCACCCTCTAATAA-3'; | 9 |
|  | 5'-TGGTTGGAGGTTGATTTAGGTGG-3'; | 10 |
| Wild type p15 | 5'-TCTGGCCGCAGGGTGCG-3'; | 11 |
|  | 5'-CCGGCCGCTCGGCCACT-3'; | 12 |
| Methylated p15 | 5'-AACCGCAAAATACGAACGC-3'; | 13 |
|  | 5'-TCGGTCGTTCGGTTATTGTACG-3'; | 14 |
| Unmethylated p15 | 5'-AACCACAAAATACAAACACATCACA-3'; | 15 |
|  | 5'-TTGGTTGTTTGGTTATTGTATGG-3'; | 16 |
| Methylated VHL | 5'-GCGTACGCAAAAAAATCCTCCA-3'; | 17 |
|  | 5'-TTCGCGGCGTTCGGTTC-3'; | 18 |
| Unmethylated VHL | 5'-ACATACACAAAAAAATCCTCCAAC-3'; | 19 |
|  | 5'-TTTGTGGTGTTTGGTTTGGG-3'; | 20 |
| Methylated E-cadherin | 5'-ACGCGATAACCCTCTAACCTAA-3'; | 21 |
|  | 5'-GTCGGTAGGTGAATTTTTAGTTA-3'; | 22 |
| Unmethylated E-cadherin | 5'-ACAATAACCCTCTAACCTAAAATTA-3'; | 23 |
|  | 5'-TGTGTTGTTGATTGGTTGTG-3'; | 24 |
| Methylated Androgen Receptor | 5'-GCGACCTCTAAATACCTAAAACCC-3'; | 25 |
|  | 5'-CGTAGAGGTTTTATAGGTTATTTGGA-3'; | 26 |
| Unmethylated Androgen Receptor | 5'-ACAACCTCTAAATACCTAAAACCC-3'; | 27 |

-continued

| | | SEQ ID NO |
|---|---|---|
| | 5'-TGTAGAGGTTTTATAGGTTATTTGGT-3'; | 28 |
| Methylated Estrogen Receptor | 5'-GACGAACTTACTACTATCCAAATACAC-3';<br>5'-TTTACGGTTAGATCGGTTTTTTTTACG-3'; | 29<br>30 |
| Unmethylated Estrogen Receptor | 5'-AACAAACTTACTACTATCCAAATACACC-3';<br>5'-TGGTTAGATTGGTTTTTTTTATGG-3'; | 31<br>32 |
| Methylated MDGI | 5'-GCCCCCGACTCCCGAAATAAA-3';<br>5'-CGTCGTCGGAGTTTTTGTACGTT-3'; | 33<br>34 |
| Unmethylated MDGI | 5'-ACCCCCAACTCCCAAAATAAAAAA-3';<br>5'-TGTTGTTGGAGTTTTTGTATGTTT-3'; | 35<br>36 |
| Methylated GSTp | 5'-GACGACCGCTACACCCCGAA-3';<br>5'-CGTCGTGATTTTAGTATTGGGGC-3'; | 37<br>38 |
| Unmethylated GSTp | 5'-AACAACCACTACACCCCAAACATC-3';<br>5'-TGTTGTGATTTTAGTATTGGGTGG-3'; | 39<br>40 |
| Methylated Calcitonin | 5'-GCCAACGACTACTCTTATTCCCG-3';<br>5'-CGTCGTCGTTTTATAGGGTTTTG-3'; | 41<br>42 |
| Unmethylated Calcitonin | 5'-ACCAACAACTACTCTTATTCCCACC-3';<br>5'-TGTTGTTGTTTTATAGGGTTTTGG-3'; | 43<br>44 |
| Methylated HIC-1 | 5'-GACGCACAACCGACTACGAC-3';<br>5'-TGGTGTTAGGGTGGGTATTGTG-3'; | 45<br>46 |
| Unmethylated HIC-1 | 5'-AACACACAACCAACTACAACCC-3';<br>5'-TGGTGTTAGGGTGGGTATTGTG-3'; | 47<br>48 |
| Methylated Endothelin | 5'-GCGTAACCAAAAAAAATAATAATATAC-3';<br>5'-CGCGTTGGTGAGTTATGA-3'; | 49<br>50 |
| Unmethylated Endothelin | 5'-ACATAACCAAAAAAAATAAATAATATACAA-3';<br>5'-TGTGTTGGTGAGTTATGAGTGTTAAG-3'; | 51<br>52 |
| Methylated TIMP-2 | 5'-GACCGCGCTACCTTCTACGAATAT-3';<br>5'-CGCGGGAGGGGTTCGTT-3'; | 53<br>54 |
| Unmethylated TIMP-2 | 5'-AACCACACTACCTTCTACAAATATATTTACTA-3';<br>5'-TGTGGGAGGGGTTTGTTTTG-3'; | 55<br>56 |
| Methylated MLH1-a | 5'-GCGACCCTAATAAAACGTCTACGT-3';<br>5'-CGCGGGTAGTTACGATGAGG-3'; | 57<br>58 |
| Unmethylated MLH1-a | 5'-ACAACCCTAATAAAACATCTACATCAAAA-3';<br>5'-TGTGGGTAGTTATGATGAGGTGGT-3'; | 59<br>60 |
| Methylated MLH1-b | 5'-GAACGACATTTTAACGCCAAAAA-3';<br>5'-CGGCGGGGGAAGTTATTTA-3'; | 61<br>62 |
| Unmethylated MLH1-b | 5'-AAACAACATTTTAACACCAAAAAAACC-3';<br>5'-TGGTGGGGGAAGTTATTTAGTGG-3'; | 63<br>64 |
| Methylated MSH2 | 5'-GAACGACGTCCGACCACGA-3';<br>5'-CGGTGTAGTCGAAGGAGACGTTG-3'; | 65<br>66 |
| Unmethylated MSH2 | 5'-AAACAACATCCAACCACAACAACC-3';<br>5'-TGGTGTAGTTGAAGGAGATGTTGTAGTTG-3'; | 67<br>68 |
| Methylated GFAP | 5'-GATACCCGAATACCCCTAACAAC-3';<br>5'-CGTCGTTTTTACGTTTTTTTAGGG-3'; | 69<br>70 |
| Unmethylated GFAP | 5'-AATACCCAAATACCCCTAACAACA-3';<br>5'-TGTTGTTTTTATGTTTTTTAGGGGA-3'; | 71<br>72 |
| Methylated TGFb1 | 5'-GCGAACTACCAAACGAACCCA-3';<br>5'-CGCGGCGGTTAGGGAGG-3'; | 73<br>74 |
| Unmethylated TGFb1 | 5'-ACAAACTACCAAACAAACCCAACC-3';<br>5'-TGTGGTGGTTAGGGAGGTGGG-3'; | 75<br>76 |
| Methylated TGFb2 | 5'-GCGCGAAAATATCGTCG-3';<br>5'-CGCGTTTCGTCGGTTT-3'; | 77<br>78 |

-continued

| | | SEQ ID NO |
|---|---|---|
| Unmethylated TGFb2 | 5'-ACACAAAAATATCATCACTCCATAC-3';<br>5'-TGTGTTTTGTTGGTTTTTAGGT-3'; | 79<br>80 |
| Methylated p130 | 5'-GACGCTAACCGCCTACAAACA-3';<br>5'-CGGTCGTTTAGGGGTGCGT-3'; | 81<br>82 |
| Unmethylated p130 | 5'-AACACTAACCACCTACAAACACCCA-3';<br>5'-TGGTTGTTTAGGGGTGTGTTATGTT-3'; | 83<br>84 |
| Methylated BRCA2 | 5'-GACTCCGCCTCTACCGC-3';<br>5'-CGGTTTTTGTTAGTTTATTTCG-3'; | 85<br>86 |
| Unmethylated BRCA2 | 5'-AACTCCACCTCTACCACCTAAT-3';<br>5'-TGGTTTTTGTTAGTTTATTTTGG-3'; | 87<br>88 |
| Methylated O6-MGMT | 5'-GCGCGAAAACGAAACCGA-3';<br>5'-CGCGTTTCGGATATGTTGGG-3'; | 89<br>90 |
| Unmethylated O6-MGMT | 5'-ACACAAAAACAAAACCAAAACAC-3';<br>5'-TGTGTTTTGGATATGTTGGGA-3'; | 91<br>92 |
| Methylated NF1 | 5'-GAACGTCCCTCAACGCCGTAA-3';<br>5'-CGTATGCGCGGTAGGTCGTTT-3'; | 93<br>94 |
| Unmethylated NF1 | 5'-AAACATCCCTCAACACCATAAAACTC-3';<br>5'-TGTATGTGTGGTAGGTTGTTTTTTTTTT3'; | 95<br>96 |
| Methylated NF2 | 5'-GCGAAACTCAAACCCGAAAC-3';<br>5'-CGTTTATCGTGAGGATCGTTATTAT-3'; | 97<br>98 |
| Unmethylated NF2 | 5'-ACAAAACTCAAACCCAAAACCC-3';<br>5'-TGTTTATTGTGAGGATTGTTATTATGG-3'; | 99<br>100 |
| Methylated TSG101 | 5'-GCTACTAAACTACCCCAAACCGTC-3';<br>5'-CGGTCGTTATGGCGGTGTC-3'; | 101<br>102 |
| Unmethylated TSG101 | 5'-ACTACTAAACTACCCCAAACCATCC-3';<br>5'-TGGTTGTTATGGTGGTGTTGGAG-3'; | 103<br>104 |

Exemplary primer pairs included in the invention that hybridize to the above sequences include:

| | SEQ ID NO: |
|---|---|
| 5'-CAGAGGGTGGGGCGGACCGC-3' and | 105 |
| 5'-CGGGCCGCGGCCGTGG-3'; | 106 |
| 5'-TTATTAGAGGGTGGGGCGGATCGC-3' and | 107 |
| 5'-GACCCCGAACCGCGACCGTAA-3'; | 108 |
| 5'-TTATTAGAGGGTGGGGTGGATTGT-3' and | 109 |
| 5'-CAACCCCAAACCACAACCATAA-3'; | 110 |
| 5'-TACCTTATTAGAGGGTGGGGCGGATCGC-3' and | 111 |
| 5'-CCACCTAAATCGACCTTCGACCG-3'; | 112 |
| 5'-TTATTAGAGGGTGGGGTGGATTGT-3' and | 113 |
| 5'-CCACCTAAATCAACCTCCAACCA-3'; | 114 |
| 5'-CGCACCCTGCGGCCAGA-3' and | 115 |
| 5'-AGTGGCCGAGCGGCCGG-3'; | 116 |
| 5'-GCGTTCGTATTTTGCGGTT-3';and | 117 |
| 5'-CGTACAATAACCGAACGACCGA-3'; | 118 |
| 5'-TGTGATGTGTTTGTATTTTGTGGTT-3' and | 119 |
| 5'-CCATACAATAACCAAACAACCAA-3'; | 120 |
| 5'-TGGAGGATTTTTTTGCGTACGC-3' and | 121 |
| 5'-GAACCGAACGCCGCGAA-3'; | 122 |
| 5'-GTTGGAGGATTTTTTTGTGTATGT-3' and | 123 |
| 5'-CCCAAACCAAACACCACAAA-3'; | 124 |
| 5'-TTAGGTTAGAGGGTTATCGCGT-3' and | 125 |
| 5'-TAACTAAAAATTCACCTACCGAC-3'; | 126 |
| 5'-TAATTTTAGGTTAGAGGGTTATTGT-3' and | 127 |
| 5'-CACAACCAATCAACAACACA-3' | 128 |
| 5'GGGTTTTAGGTATTTAGAGGTCGC-3' and | 129 |
| 5'ACCAAATAACCTATAAAACCTCTACG-3' | 130 |
| 5'GGGTTTTAGGTATTTAGAGGTTGT-3' and | 131 |
| 5'ACCAAATAACCTATAAAACCTCTACA-3' | 132 |

| | SEQ ID NO: |
|---|---|
| 5'GTGTATTTGGATAGTAGTAAGTTCGTC-3' and | 133 |
| 5'CGTAAAAAAAACCGATCTAACCGTAAA-3' | 134 |
| 5'GGTGTATTTGGATAGTAGTAAGTTTGTT-3' and | 135 |
| 5'CCATAAAAAAAACCAATCTAACCA-3' | 136 |
| 5'TTTATTTCGGGAGTCGGGGGC-3' and | 137 |
| 5'AACGTACAAAAACTCCGACGACG-3' | 138 |
| 5'TTTTTTATTTTGGGAGTTGGGGGT-3' and | 139 |
| 5'AAACATACAAAAACTCCAACAACA-3' | 140 |
| 5'TTCGGGGTGTAGCGGTCGTC-3' and | 141 |
| 5'GCCCCAATACTAAAATCACGACG-3' | 142 |
| 5'GATGTTGGGGTGTAGTGGTTGTT-3' and | 143 |
| 5'CCACCCCAATACTAAAATCACAACA-3' | 144 |
| 5'CGGGAATAAGAGTAGTCGTTGGC-3'and | 145 |
| 5'CAAAACCCTATAAAAACGACGACG-3' | 146 |
| 5'GGTGGGAATAAGAGTAGTTGTTGGT-3'and | 147 |
| 5'CCAAAACCCTATAAAAACAACAACA-3' | 148 |
| 5'GTCGTAGTCGGTTGTGCGTC-3'and | 149 |
| 5'GATACCCGCCCTAACGCCG-3 | 150 |
| 5'GGGTTGTAGTTGGTTGTGTGTT-3'and | 151 |
| 5'CACAATACCCACCCTAACACCA-3' | 152 |
| 5'GTATATTATTTATTTTTTTGGTTACGC-3'and | 153 |
| 5'TCATAACTCGCCAACGCG-3' | 154 |
| 5'TTGTATATTATTTATTTTTTTGGTTATGT-3'and | 155 |
| 5'CTTAACACTCATAACTCACCAACACA-3' | 156 |
| 5'ATATTCGTAGAAGGTAGCGCGGTC-3'and | 157 |
| 5'AACGAACCCCTCCCGCG-3' | 158 |
| 5'TAGTAAATATATTTGTAGAAGGTAGTGTGGTT-3'and | 159 |
| 5'CAAAACAAACCCCTCCCACA-3' | 160 |
| 5'ACGTAGACGTTTTTATTAGGGTCGC-3'and | 161 |
| 5'CCTCATCGTAACTACCCGCG-3' | 162 |
| 5'TTTTGATGTAGATGTTTTATTAGGGTTGT-3'and | 163 |
| 5'ACCACCTCATCATAACTACCCACA-3' | 164 |
| 5'TTTTTGGCGTTAAAATGTCGTTC-3'and | 165 |
| 5'TAAATAACTTCCCCCGCCG-3' | 166 |
| 5'GGTTTTTTTGGTGTTAAAATGTTGTTT-3'and | 167 |
| 5'CCACTAAATAACTTCCCCCACCA-3' | 168 |
| 5'TCGTGGTCGGACGTCGTTC-3'and | 169 |
| 5'CAACGTCTCCTTCGACTACACCG-3' | 170 |

| | SEQ ID NO: |
|---|---|
| 5'GGTTGTTGTGGTTGGATGTTGTTT-3'and | 171 |
| 5'CAACTACAACATCTCCTTCAACTACACCA-3' | 172 |
| 5'GTTGTTAGGGGTATTCGGGTATC-3'and | 173 |
| 5'CCCTAAAAAAACGTAAAAACGACG-3' | 174 |
| 5'TGTTGTTAGGGGTATTTGGGTATT-3'and | 175 |
| 5'TCCCCTAAAAAAACATAAAAACAACA-3' | 176 |
| 5'TGGGTTCGTTTGGTAGTTCGC-3'and | 177 |
| 5'CCTCCCTAACCGCCGCG-3' | 178 |
| 5'GGTTGGGTTTGTTTGGTAGTTTGT-3'and | 179 |
| 5'CCCACCTCCCTAACCACCACA-3' | 180 |
| 5'CGACGATATTTTCGCGC-3'and | 181 |
| 5'AAACCGACGAAACGCG-3' | 182 |
| 5'GTATGGAGTGATGATATTTTTGTGT-3'and | 183 |
| 5'ACCTAAAAACCAACAAAACACA-3' | 184 |
| 5'TGTTTGTAGGCGGTTAGCGTC-3' and | 185 |
| 5'ACGCACCCCTAAACGACCG-3' | 186 |
| 5'TGGGTGTTTGTAGGTGGTTAGTGTT | 187 |
| 5'AACATAACACACCCCTAAACAACCA-3' | 188 |
| 5'GCGGTAGAGGCGGAGTC-3'and | 189 |
| 5'CGAAATAAACTAACAAAAACCG-3' | 190 |
| 5'ATTAGGTGGTAGAGGTGGAGTT-3'and | 191 |
| 5'CCAAAATAAACTAACAAAAACCA-3' | 192 |
| 5'TCGGTTTCGTTTTCGCGC-3'and | 193 |
| 5'CCCAACATATCCGAAACGCG-3 | 194 |
| 5'GTGTTTTGGTTTTGTTTTTGTGT-3'and | 195 |
| 5'TCCCAACATATCCAAAACACA-3' | 196 |
| 5'TTACGGCGTTGAGGGACGTTC-3'and | 197 |
| 5'AAACGACCTACCGCGCATACG-3' | 198 |
| 5'GAGTTTTATGGTGTTGAGGGATGTTT-3'and | 199 |
| 5'AAAAAAAAAAACAACCTACCACACATACA-3' | 200 |
| 5'GTTTCGGGTTTGAGTTTCGC-3'and | 201 |
| 5'ATAATAACGATCCTCACGATAAACG-3' | 202 |
| 5'GGGTTTTGGGTTGAGTTTTGT-3'and | 203 |
| 5'CCATAATAACAATCCTCACAATAAACA-3' | 204 |
| 5'GACGTTTGGGGTAGTTTAGTAGC-3'and | 205 |
| 5'GACACCGCCATAACGACCG-3' | 206 |
| 5'GGATGGTTTGGGGTAGTTTAGTAGT-3'and | 207 |
| 5'CTCCAACACCACCATAACAACCA-3' | 208 |

-continued

| | SEQ ID NO: |
|---|---|
| *lso included are modifications of the above sequences, including SEQ ID NO:107 having the sequence TCAC at the 5'end (SEQ ID NO:214); SEQ ID NO:107 having the sequence CC added at the 5'end (SEQ ID NO:215); SEQ ID NO:107 having the sequence 5'-TTATTAGAGGGTGGGGCGGATCGC-3'; SEQ ID NO:108 having the sequence 5'-GACCCCGAACCGCGACCGTAA-3';SEQ ID NO:110 having the sequence TGG added at the 5'end (SEQ ID NO:216); and SEQ ID. All of these modified primers anneal at 65° C. | |

Typically, the CpG-containing nucleic acid is in the region of the promoter of a structural gene. For example, the promoter region of tumor suppressor genes have been identified as containing methylated CpG island. The promoter region of tumor suppressor genes, including p16, p15, VHL and E-cadherin, are typically the sequence amplified by PCR in the method of the invention. Other genes that have been shown by MSP as containing methylated CpG neoplastic versus normal tissue include estrogen receptor, MDGI, GST-pi, calcitonin, HIC-1, endothelin B receptor, TIMP-2, 06-MGMT, and MLH1. Genes that were found by MSP to be methylated also include the androgen receptor (e.g., methylated as X chromosome inactivation), GFAP (methylated in some glioma cell lines but also in normal tissue), and MSH2. Other genes in which MSP primer were shown to distinguish between normal unmethylated and methylated DNA include TGF-β1, TGF-β2, p130, BRCA2, NF1, NF2, and TSG101.

Detection and identification of methylated CpG-containing nucleic acid in the specimen may be indicative of a cell proliferative disorder or neoplasia. Such disorders include but are not limited to low grade astrocytoma, anaplastic astrocytoma, glioblastoma, medulloblastoma, colon cancer, lung cancer, renal cancer, leukemia, breast cancer, prostate cancer, endometrial cancer and neuroblastoma. Identification of methylated CpG status is also useful for detection and diagnosis of genomic imprinting, fragile X syndrome and X-chromosome inactivation.

Using the method of the invention, the TIMP-2 gene was identified as associated with or methylated in neoplastic versus normal tissues.

The method of the invention now provides the basis for a kit useful for the detection of a methylated CpG-containing nucleic acid. The kit includes a carrier means being compartmentalized to receive in close confinement therein one or more containers. For example, a first container contains a reagent which modifies unmethylated cytosine, such as sodium bisulfite. A second container contains primers for amplification of the CpG-containing nucleic acid, for example, primers listed above as SEQ ID NO:105–208.

The invention also provides a kit for the detection of a methylated CpG-containing nucleic acid, wherein the kit includes: a) a reagent that modifies unmethylated cytosine nucleotides; b) control nucleic acid; c) primers for the amplification of unmethylated CpG-containing nucleic acid; d) primers for the amplification of methylated CpG-containing nucleic acid; and e) primers for the amplification of control nucleic acid. The kit may further include nucleic acid amplification buffer. Preferably, the reagent that modifies unmethylated cytosine is bisulfite.

The kit of the invention is intended to provide the reagents necessary to perform chemical modification and PCR amplification of DNA samples to determine their methylation status. The primer sets included in the kit include a set that anneals to unmethylated DNA that has undergone a chemical modification; a set that anneals to methylated DNA that has undergone a chemical modification; and a primer set that serves as a control for the efficiency of chemical modification. The control primer set should anneal to any DNA (unmethylated or methylated) that has not undergone chemical methylation. In the case of incomplete chemical modification (up to about 50%), data interpretation can still proceed.

The above disclosure generally describes the present invention. A more complete understanding can be obtained by reference to the following specific examples which are provided herein for purposes of illustration only and are not intended to limit the scope of the invention.

EXAMPLE 1

DNA and Cell Lines. Genomic DNA was obtained from cell lines, primary tumors and normal tissue as described (Merlo, et al., *Nature Medicine*, 1:686, 1995; Herman, et al., *Cancer Research*, 56:722, 1996; Graff, et al., *Cancer Research*, 55:5195, 1995). The renal carcinoma cell line was kindly provided by Dr. Michael Lehrman of the National Cancer Institute, Bethesda, Md.

Bisulfite Modification. 1 μg of DNA in a volume of 50 μl was denatured by NaOH (final 0.2M) for 10 minutes at 37° C. For samples with nanogram quantities of human DNA, 1 μg of salmon sperm DNA (Sigma) was added as carrier prior to modification. 30 μL of 10 mM hydroquinone (Sigma) and 520 μL of 3 M sodium bisulfite (Sigma) pH5, both freshly prepared, were added, mixed, and samples were incubated under mineral oil at 50° C. for 16 hours. Modified DNA was purified using the Wizard™ DNA purification resin according to the manufacturer (Promega), and eluted into 50 μL of water. Modification was completed by NaOH (final 0.3M) treatment for 5 minutes at room temperature, followed by ethanol precipitation.

Genomic Sequencing. Genomic sequencing of bisulfite modified DNA was accomplished using the solid-phase DNA sequencing approach (Myohanen, et al., DNA Seq., 5:1, 1994). 100 ng of bisulfite modified DNA was amplified with p16 gene specific primer 5'-TTTTTAGAGGATTTGAGGGATAGG-3' (sense) (SEQ ID NO:209) and 5'-CTACCTAATTCCAATTCCCCTACA-3' (anti-sense) (SEQ ID NO:210). PCR conditions were as follows: 96° C. for 3 minutes, 80° C. for 3 minutes, 1 U of Taq polymerase (BRL) was added, followed by 35 cycles of 96° C. for 20 seconds, 56° C. for 20 seconds, 72° C. for 90 seconds, followed by 5 minutes at 72° C. The PCR mixture contained 1× buffer (BRL) with 1.5 mM $MgCl_2$, 20 pmols of each primer and 0.2 mM dNTPs. To obtain products for sequencing, a second round of PCR was performed with 5 pmols of nested primers. In this reaction, the sense primer, 5'-GTTTTCCCAGTCACGACAGTATTAGGAGGAA-GAAAGAGGAG-3' (SEQ ID NO:211), contains M13–40 sequence (underlined) introduced as a site to initiate sequencing, and the anti-sense primer 5'-TCCAATTCCCCTACAAACTTC-3" (SEQ ID NO:212) is biotinylated to facilitate purification of the product prior to sequencing. PCR was performed as above, for 32 cycles with 2.5 mm $MgCl_2$. All primers for genomic sequencing were designed to avoid any CpGs in the sequence. Biotinylated PCR products were purified using streptavidin coated magnetic beads (Dynal AB, Norway), and sequencing reactions performed with Sequenase™ and M13–40 sequencing primer under conditions specified by the manufacturer (USB).

PCR Amplification. Primer pairs described in Table 1 were purchased from Life Technologies. The PCR mixture contained 1× PCR buffer (16.6 mM ammonium sulfate, 67 mM TRIS pH 8.8, 6.7 mM $MgCl_2$, and 10 mM β-mercaptoethanol), dNTPs (each at 1.25 mM), primers (300 ng/reaction each), and bisulfite-modified DNA (~50 ng) or unmodified DNA (50–110 ng) in a final volume of 50 µL. PCR specific for unmodified DNA also included 5% dimethylsulfoxide. Reactions were hot started at 95° C. for 5 minutes prior to the addition of 1.25 units of Taq polymerase (BRL). Amplification was carried out on a Hybaid OmniGene temperature cycler for 35 cycles (30 seconds at 95° C., 30 seconds at the annealing temperature listed in Table 1, and 30 seconds at 72° C.), followed by a final 4 minute extension at 72° C. Controls without DNA were performed for each set of PCR reactions. 10 µL of each PCR reaction was directly loaded onto non-denaturing 6–8% polyacrylamide gels, stained with ethidium bromide, and directly visualized under UV illumination.

Restriction Analysis. 10 µL of the 50 µL PCR reaction was digested with 10 units of BstUI (New England Biolabs) for 4 hours according to conditions specified by the manufacturer. Restriction digests were ethanol precipitated prior to gel analysis.

EXAMPLE 2

An initial study was required to validate the strategy for MSP for providing assessment of the methylation status of CpG islands. The p16 tumor suppressor (Merlo, et al., supra; Herman, et al., *Cancer Research*, 55:4525, 1995; Gonzalez-Zulueta, et al., *Cancer Res.*, 55:4531, 1995,27) which has been documented to have hypermethylation of a 5' CpG island is associated with complete loss of gene expression in many cancer types, was used as an exemplary gene to determine whether the density of methylation, in key regions to be tested, was great enough to facilitate the primer design disclosed herein. Other than for CpG sites located in recognition sequences for methylation-sensitive enzymes, the density of methylation and its correlation to transcriptional silencing had not yet been established. The genomic sequencing technique was therefore employed to explore this relationship.

FIG. 1 shows genomic sequencing of p16. The sequence shown has the most 5' region at the bottom of the gel, beginning at +175 in relation to a major transcriptional start site (Hara, et al., *Mol. Cell Biol.*, 16:859, 1996). All cytosines in the unmethylated cell line H249 have been converted to thymidine, while all C's in CpG dinucleotides in the methylated cell H157 remains as C, indicating methylation.] enclosed a BstUI site which is at −59 in relation to the transnational start site in Genbank sequence U12818 (Hussussian, et al., *Nat. Genet.*, 8:15, 1994), but which is incorrectly identified as CGCA in sequence X94154 (Hara, et al., supra). This CGCG site represents the 3' location of the sense primer used for p16 MSP.

As has been found for other CpG islands examined in this manner (Myohanen, et al., supra; Park, et al., *Mol. Cell Biol.*, 14:7975, 1994; Reeben, et al., *Gene*, 157:325, 1995), the CpG island of p16 was completely unmethylated in those cell lines and normal tissues previously found to be unmethylated by Southern analysis (FIG. 1)(Merlo, et al., supra; Herman, et al., supra). However, it was extensively methylated in cancer cell lines shown to be methylated by Southern analysis (FIG. 1). In fact, all cytosines within CpG dinucloetides in this region were completely methylated in the cancers lacking p16 transcription. This marked difference in sequence following bisulfite treatment suggested that the method of the invention for specific amplification of either methylated or unmethylated alleles was useful for identification of methylation patterns in a DNA sample.

Primers were designed to discriminate between methylated and unmethylated alleles following bisulfite treatment, and to discriminate between DNA modified by bisulfite and that which had not been modified. To accomplish this, primer sequences were chosen for regions containing frequent cytosines (to distinguish unmodified from modified DNA), and CpG pairs near the 3' end of the primers (to provide maximal discrimination in the PCR reaction between methylated and unmethylated DNA). Since the two strands of DNA are no longer complementary after bisulfite treatment, primers can be designed for either modified strand. For convenience, primers were designed for the sense strand. The fragment of DNA to be amplified was intentionally small, to allow the assessment of methylation patterns in a limited region and to facilitate the application of this technique to samples, such as paraffin blocks, where amplification of larger fragments is not possible. In Table 1, primer sequences are shown for all genes tested, emphasizing the differences in sequence between the three types of DNA which are exploited for the specificity of MSP. The multiple mismatches in these primers which are specific for these different types of DNA suggest that each primer set should provide amplification only from the intended template.

The primers designed for p16 were tested with DNA from cancer cell lines and normal tissues for which the methylation status had previously been defined by Southern analysis (Merlo, et al., supra; Herman, et al., supra).

FIG. 2, panels A–D, show polyacrylamide gels with the Methylation Specific PCR products of p16. Primer sets used for amplification are designated as unmethylated (U), methylated (M), or unmodified/wild-type (W). * designates the molecular weight marker pBR322-MspI digest. Panel A shows amplification of bisulfite-treated DNA from cancer cell lines and normal lymphocytes, and untreated DNA (from cell line H249). Panel B shows mixing of various amount of H157 DNA with 1 µg of H249 DNA prior to bisulfite treatment to assess the detection sensitivity of MSP for methylated alleles. Modified DNA from a primary lung cancer sample and normal lung are also shown. Panel C shows amplification with the p16-U2 (U) primers, and p16-M2 (M) described in Table 1. Panel D shows the amplified p16 products of panel C restricted with BstUI(+) or not restricted (−).

In all cases, the primer set used confirmed the methylation status determined by Southern analysis. For example, lung cancer cell lines U1752 and H157, as well other cell lines methylated at p16, amplified only with the methylated primers (FIG. 2, panel A). DNA from normal tissues (lymphocytes, lung, kidney, breast, and colon) and the unmethylated lung cancer cell lines H209 and H249, amplified only with unmethylated primers (examples in FIG. 2, panel A). PCR with these primers could be performed with or without 5% DMSO. DNA not treated with bisulfite (unmodified) failed to amplify with either set of methylated or unmethylated specific primers, but readily amplified with primers specific for the sequence prior to modification (FIG. 2, panel A). DNA from the cell line H157 after bisulfite treatment also produced a weaker amplification with unmodified primers, suggesting an incomplete bisulfite reaction. However, this unmodified DNA, unlike partially restricted DNA in previous PCR assays relying on methylation sensitive restriction enzymes, is not recognized by the primers specific for methylated DNA. It therefore does not provide a false positive result or interfere with the ability to distinguish methylated from unmethylated alleles.

The sensitivity of MSP for detection of methylated p16 alleles was assessed. DNA from methylated cell lines was mixed with unmethylated DNA prior to bisulfite treatment. 0.1% of methylated DNA (approximately 50 pg) was consistently detected in an otherwise unmethylated sample (FIG. 2, panel B). The sensitivity limit for the amount of input DNA was determined to be as little as 1 ng of human DNA, mixed with salmon sperm DNA as a carrier detectable by MSP.

Fresh human tumor samples often contain normal and tumor tissue, making the detection of changes specific for the tumor difficult. However, the sensitivity of MSP suggests it would be useful for primary tumors as well, allowing for detection of aberrantly methylated alleles even if they contribute relatively little to the overall DNA in a sample. In each case, while normal tissues were completely unmethylated, tumors determined to be methylated at p16 by Southern analysis also contained methylated DNA detected by MSP, in addition to some unmethylated alleles (examples in FIG. 2, panel B). DNA from paraffin-embedded tumors was also used, and allowed the detection of methylated and unmethylated alleles in these samples (FIG. 2, panel B). To confirm that these results were not unique to this primer set, a second downstream primer for p16 was used which would amplify a slightly larger fragment (Table 1). This second set of primers reproduced the results described above (FIG. 2, panel C), confirming the methylation status defined by Southern blot analysis.

To further verify the specificity of the primers for the methylated alleles and to check specific cytosines for methylation within the region amplified, the differences in sequence between methylated/modified DNA and unmethylated/modified DNA were utilized. Specifically, the BstUI recognition site, CGCG, will remain CGCG if both C's are methylated after bisulfite treatment and amplification, but will become TGTG if unmethylated. Digestion of the amplified products with BstUI distinguishes these two products. Restriction of p16 amplified products illustrates this. Only unmodified products and methylated/modified products, both of which retain the CGCG site, were cleaved by BstUI, while products amplified with unmethylated/modified primers failed to be cleaved (FIG. 2, panel D).

The primer sets discussed above were designed to discriminate heavily methylated CpG islands from unmethylated alleles. To do this, both the upper (sense) and lower (antisense) primers contained CpG sites which could produce methylation-dependent sequence differences after bisulfite treatment. MSP might be employed to examine more regional aspects of CpG island methylation. To examine this, methylation-dependent differences in the sequence of just one primer was tested to determine whether it would still allow discrimination between unmethylated and methylated p16 alleles. The antisense primer used for genomic sequencing, 5'-CTACCTAATTCCAATTCCCCTACA-3' (SEQ ID NO:213), was also used as the antisense primer, since the region recognized by the primer contains no CpG sites, and was paired with either a methylated or unmethylated sense primer (Table 1). Amplification of the 313 bp PCR product only occurred with the unmethylated sense primer in H209 and H249 (unmethylated by Southern) and the methylated sense primer in H157 and U1752 (methylated by Southern), indicating that methylation of CpG sites within a defined region can be recognized by specific primers and distinguish between methylated and unmethylated alleles (FIG. 2, panel E). Panel E shows results of testing for regional methylation of CpG islands with MSP, using sense primers p16-U2 (U) and p16-M2 (M), which are methylation specific, and an antisense primer which is not methylation specific.

EXAMPLE 3

The above experiments with p16 were extended to include 3 other genes transcriptionally silenced in human cancers by aberrant hypermethylation of 5' CpG islands.

FIG. 3, panels A–E, show polyacrylamide gels of MSP products from analysis of several genes. Primer sets used for amplification are not designated as unmethylated (U), methylated (M), or unmodified/wild-type (W). * designates the molecular weight marker pBR322-MspI digest and ** designates the 123 bp molecular weight marker. All DNA samples were bisulfite treated except those designated untreated. Panel A shows the results from MSP for p15. Panel B shows the p15 products restricted with BstUI (+) or not restricted (−). Panel C shows the products of MSP for VHL. Panel D shows the VHL products restricted with BstUI(+) or not restricted (−). Panel E shows the products of MSP for E-cadherin.

The cyclin-dependent kinase inhibitor p15 is aberrantly methylated in many leukemic cell lines and primary leukemias (Herman, et al., supra). For p15, MSP again verified the methylation status determined by Southern analysis. Thus, normal lymphocytes and cancer cell lines SW48 and U1752, all unmethylated by Southern analysis (Herman, et al., supra), only amplified with the unmethylated set of primers, while the lung cancer cell line H1618 and leukemia cell line KG1A amplified only with the methylated set of primers (FIG. 3, panel A), consistent with previous Southern analysis results (Herman, et al., supra). The cell line Raji produced a strong PCR product with methylated primers and a weaker band with unmethylated primers. This was the same result for methylation obtained previously by Southern analysis (Herman, et al., supra). Non-cultured leukemia samples, like the primary tumors studied for p16, had amplification with the methylated primer set as well as the unmethylated set. This heterogeneity also matched Southern analysis (Herman, et al., supra). Again, as for p16, differential modification of BstUI restriction sites in the amplified product of p15 was used to verify the specific amplification by MSP (FIG. 3, panel B). Amplified products using methylated primer sets from cell lines H1618 and Raji or unmodified primer sets, were completely cleaved by BstUI, while unmethylated amplified products did not cleave. Primary AML samples, which again only demonstrated cleavage in the methylated product, had less complete cleavage. This suggests a heterogeneity in methylation, arising because in some alleles, many CpG sites within the primer sequences area are methylated enough to allow the methylation specific primers to amplify this region, while other CpG sites are not completely methylated.

Aberrant CpG island promoter region methylation is associated with inactivation of the VHL tumor suppressor gene in approximately 20% of clear renal carcinomas (Herman, et al., *Proc. Natl. Acad. Sci. USA*, 91:9700, 1994). This event, like mutations for VHL (Gnarra, et al., *Nature Genetics*, 7:85, 1994), is restricted to clear renal cancers (Herman, et al., supra). Primers designed for the VHL sequence were used to study DNA from the renal cell cancer line RFX393 which is methylated at VHL by Southern analysis, and the lung cancer cell line U1752 which is unmethylated at this locus (Herman, et al., supra). In each case, the methylation status of VHL determined by MSP confirmed that found by Southern analysis (FIG. 3, panel C), and BstUI restriction site analysis validated the PCR product specificity (FIG. 3, panel D).

The expression of the invasion/metastasis suppressor gene, E-cadherin, is often silenced by aberrant methylation of the 5' promoter in breast, prostate, and many other carcinomas (Graff, et al., supra; Yoshira, et al., *Proc. Natl. Acad. Sci. USA*, 92:7416, 1995). Primers were designed for the E-cadherin promoter region to test the use of MSP for this gene. In each case, MSP analysis paralleled Southern blot analysis for the methylation status of the gene (Graff, et al., supra). The breast cancer cell lines MDA-MB-231, HS578t, and the prostate cancer cell lines DuPro and TSUPrI, all heavily methylated by Southern, displayed prominent methylation. MCF7, T47D, PC-3, and LNCaP, all unmethylated by Southern, showed no evidence for methylation in the sensitive MSP assay (FIG. 3, panel E). MSP analysis revealed the presence of unmethylated alleles in Hs578t, TSUPrI and DuPro consistent with a low percentage of unmethylated alleles in these cell lines previously detected by Southern analysis (Graff, et al., supra). BstUI restriction analysis again confirmed the specificity of the PCR amplification.

TABLE 1

PCR primers used for Methylation Specific PCR

| Primer Set | Sense primer* (5'—3') | Antisense primer* (5'—3') | Size (bp) | Anneal temp. | Genomic Position† |
|---|---|---|---|---|---|
| p16-W† | CAGAGGGTGGGGCGACCGC | CGGGCCGCGGCCGTGG | 140 | 65° C. | +171 |
| p16-M | TTATTAGAGGGTGGGGCGGATCGC | GACCCCGAACCGCGACCGTAA | 150 | 65° C. | +167 |
| p16-U | TTATTAGAGGGTGGGGTGGATTGT | CAACCCCAAACCACAACCATAA | 151 | 65° C. | +167 |
| p16-M2 | TTATTAGAGGGTGGGGCGGATCGC | CCACCTAAATCGACCTCCGACCG | 234 | 65° C. | +167 |
| p16-U2 | TTATTAGAGGGTGGGGTGGATTGT | CCACCTAAATCAACCTCCAACCA | 234 | 60° C. | +167 |
| p15-W | CGCACCCTGCGGCCAGA | AGTGGCCGAGCGGCCGG | 137 | 65° C. | +46 |
| p15-M | GCGTTCGTATTTTGCGGTT | CGTACAATAACCGAACGACCGA | 148 | 60° C. | +40 |
| p15-U | TGTGATGTGTTTGTATTTTGTGGTT | CCATACAATAACCAAACAACCAA | 154 | 60° C. | +34 |
| VHL-M | TGGAGGATTTTTTTGCGTACGC | GAACCGAACGCCGCGAA | 158 | 60° C. | −116 |
| VHL-U | GTTGGAGGATTTTTTTGTGTATGT | CCCAAACCAAACACCACAAA | 165 | 60° C. | −118 |
| Ecad-M0 | TTAGGTTAGAGGGTTATCGCGT | TAACTAAAAATTCACCTACCGAC | 116 | 57° C. | +205 |
| Ecad-U | TAATTTTAGGTTAGAGGGTTATTGT | CACAACCAATCAACAACACA | 97 | 53° C. | −210 |

*Sequence differences between modified primers and unmodified DNA are boldface, and differences between methylated/modified and unmethylated/modified are underlined.
†Primers were placed near the transcriptional strat site. Genomic position is the location of the 5' nucleotide of the sense primer in relation to the major transcriptional start site defined in the following references and Genbank accession numbers: p16(most 3' site) X94154 (E. Hara, et al., Mol. Cell Biol., 16: 859 1996), p15 S75756 (J. Jen, et al., Cancer Res., 54: 6353 1994), VHL U19763 (I. Kuzmin, et al., Oncogene, 10: 2185 1995), and E-cadherin L34545 (M. J. Bussemakers, et al., Biochem. Biophys. Res. Commun., 203: 1284 1994).
†W represents unmodified, or wild-type primers, M represents methylated-specific primers, and U represents unmethylted-specific primers.
(SEQ ID NO:105—128)

TABLE 2

| Gene | | Sense Primer | Antisense Primer | PCR Product | Temp | Genbank # | Position |
|---|---|---|---|---|---|---|---|
| Androgen Receptor | Me | 5'gggttttaggtatttagaggtcgc | 5'accaaataacctataaaacctctacg | ~210 bp | 55° C. | M27423 | 189 |
| | Un | 5'gggttttaggtatttagaggttgt | 5'accaaataacctataaaacctctaca | ~210 bp | 55° C. | M27423 | 189 |
| Estrogen Receptor | Me | 5'gtgtatttggatagtagtaagttcgtc | 5'cgtaaaaaaaaccgatctaaccgtaaa | 118 bp | 57° C. | X62462 | 3127 |
| | Un | 5'ggtgtatttggatagtagtaagtttgtt | 5'ccataaaaaaaaccaatctaacca | 120 bp | 57° C. | X62462 | 3126 |
| MDGI | Me | 5'tttatttcgggagtcgggggc | 5'aacgtacaaaaatccgacgacg | 105 bp | 60° C. | U57623 | 1134 |
| | Un | 5'tttttatttgggagttggggt | 5'aaacatacaaaaactccaacaca | 113 bp | 60° C. | U57623 | 1131 |
| GST | Me | 5'ttcggggtgtagcggtcgtc | 5'gccccaatactaaaatcacgacg | 91 bp | 60° C. | X08058 | 1082 |
| | Un | 5'gatgtttgggtgtagtggttgtt | 5'ccaccccaatactaaaatcacaaca | 97 bp | 60° C. | X08058 | 1078 |
| Calcitonin | Me | 5'cgggaataagagtagtcgttggc | 5'caaaaccctataaaaacgacgacg | 84 bp | 60° C. | X15943 | 1801 |
| | UN | 5'ggtgggaataagagtagttgttggt | 5'ccaaaaccctataaaaacaacaca | 87 bp | 60° C. | X15943 | 1799 |
| HIC-1 | Me | 5'gtcgtagtcggttgtcgtc | 5'gatacccgccctaacgccg | 259 bp | 60° C. | | |
| | Un | 5'gggttgtagttggttgtgtgtt | 5'cacaataccaccctaacacca | 264 bp | 60° C. | | |
| Endothelin | Me | 5'gtatattatttatttttttggttacgc | 5'tcataactgccaacgcg | 92 bp | 55° C. | D13162 | 969 |
| | Un | 5'ttgtatattatttatttttttggttatgt | 5'cttaacactcataactcaccaacaca | 102 bp | 55° C. | D13162 | 967 |

TABLE 2-continued

| Gene | | Sense Primer | Antisense Primer | PCR Product | Temp | Genbank # | Position |
|------|---|--------------|------------------|-------------|------|-----------|----------|
| TIMP-2 | Me | 5'atattcgtagaaggtagcgcggtc | 5'aacgaacccctccgcg | 190 bp | 59° C. | U44381 | 2254 |
| | Un | 5'tagtaaatatatttgtagaaggtagtgtggtt | 5'caaaacaaaccccctcccaca | 201 bp | 59° C. | U44381 | 2246 |
| MLH1-a | Me | 5'acgtagacgttttattagggtcgc | 5'cctcatcgtaactacccgcg | 115 bp | 60° C. | U26559 | 218 |
| | Un | 5'ttttgatgtagatgttttattagggttgt | 5'accacctcatcataactacccaca | 124 bp | 60° C. | U26559 | 213 |
| MLH1-b | ME | 5'ttttggcgttaaaatgtcgttc | 5'taaataacttcccccgccg | 91 bp | 60° C. | U26559 | 920 |
| | Un | 5'ggttttttggtgttaaaatgttgttt | 5'ccactaaataacttcccccacca | 99 bp | 60° C. | U26559 | 916 |
| MSH2 | Me | 5'tcgtggtcggacgtcgttc | 5'caacgtctccttcgactacaccg | 132 | 60° C. | U41206 | 128 |
| | Un | 5'ggttgttgtggttggatgttgttt | 5'caactacaacatctccttcaactacacca | 143 | 60° C. | U41206 | 123 |
| GFAP | Me | 5'gttgttaggggtattcgggtatc | 5'ccctaaaaaaacgtaaaaacgacg | 140 bp | 60° C. | M67446 | 2092 |
| | Un | 5'tgttgttaggggtatttgggtatt | 5'tcccctaaaaaaacataaaaacaaca | 143 bp | 60° C. | M67446 | 2091 |
| TGFβ1 | Me | 5'tgggttcgttcgttggtagttcgc | 5'cctccctaaccgccgcg | 124 bp | 57° C. | U51139 | 1223 |
| | Un | 5'ggttgggtttgtttggtagtttgt | 5'cccacctcctaaccaccaca | 131 bp | 57° C. | U51139 | 1220 |
| TGFβ2 | Me | 5'cgacgatattttcgcgc | 5'aaaccgacgaaacgcg | 97 bp | 57° C. | U52240 | 72 |
| | Un | 5'gtatggagtgatgatattttgtgt | 5'acctaaaaaccaacaaaacaca | 111 bp | 57° C. | U52240 | 64 |
| p130 | Me | 5'tgtttgtaggcggttagcgtc | 5'acgcacccctaaacgaccg | 135 bp | 55° C. | U53220 | 2076 |
| | Un | 5'tgggtgttttgtaggtggttagtgtt | 5'aacataacacacccctaaacaacca | 145 bp | 55° C. | U53220 | 2072 |
| BRCA2 | Me | 5'gcggtagaggcggagtc | 5'cgaaataaactaacaaaaccg | 136 bp | 55° C. | X95151 | 292 |
| | Un | 5'attaggtggtagaggtggagtt | 5'ccaaaataaactaacaaaaacca | 142 bp | 55° C. | X95151 | 287 |
| O⁶— | Me | 5'tcggtttcgttttcgcgc | 5'cccaacatatccgaaacgcg | 125 bp | 60° C. | S52289 | 114 |
| MGMT | Un | 5'gtgttttgttttgttttttgtgt | 5'tcccaacatatccaaaacaca | 131 bp | 60° C. | S52289 | 109 |
| NF1 | Me | 5'ttacggcgttgagggacgttc | 5'aaacgacctaccgcgcatacg | 121 bp | 60° C. | U17084 | 3336 |
| | Un | 5'gagtttttatggtgttgagggatgttt | 5'aaaaaaaaaaacaacctaccacacataca | 134 bp | 60° C. | U17084 | 3331 |
| NF2 | Me | 5'gtttcgggtttgagtttcgc | 5'ataataacgatcctcacgataaacg | 109 bp | 55° C. | L27131 | 38 |
| | Un | 5'gggttttgggtttgagttttgt | 5'ccataataacaatcctcacaataaaca | 113 bp | 55° C. | L27131 | 36 |
| TSG101 | Me | 5'gacggttgggtagtttagtagc | 5'gacaccgccataacgaccg | 80 bp | 60° C. | U82130 | 23 |
| | Un | 5'ggatggtttggggtagtttagtagt | 5'ctccaacaccaccataacaacca | 85 bp | 60° C. | U82130 | 22 |

(SEQ ID NO: 25–104)

Although the invention has been described with reference to the presently preferred embodiments, it should be understood that various modifications can be made without departing from the spirit of the invention. Accordingly, the invention is limited only by the following claims.

What is claimed is:

1. A method for detecting a methylated CpG in a 5' regulatory region of a nucleic acid sequence comprising:
   contacting a nucleic acid-containing specimen with an agent that modifies unmethylated cytosine;
   amplifying the CpG-containing nucleic acid in the specimen by means of CpG-specific oligonucleotide primers, wherein the oligonucleotide primers distinguish between modified methylated and non-methylated nucleic acid in the 5' regulatory region; and
   detecting the methylated nucleic acid based on the presence of amplification products produced in the amplifying step.

2. The method of claim 1, wherein the agent is bisulfite.

3. The method of claim 1, wherein the amplifying step is by polymerase chain reaction (PCR).

4. The method of claim 1, wherein cytosine is modified to uracil.

5. The method of claim 1, wherein the 5' regulatory region is in a promoter region.

6. The method of claim 5, wherein the promoter is a tumor suppressor gene promoter.

7. The method of claim 6, wherein the tumor suppressor gene is selected from the group consisting of p16, p15, E-cadherin, and VHL.

8. The method of claim 1, wherein the specimen is from a tissue selected from the group consisting of brain, colon, urogenital, lung, renal, hematopoietic, breast, thymus, testis, ovarian, and uterine.

9. The method of claim 1, further comprising contacting the nucleic acid with a methylation sensitive restriction endonuclease.

10. The method of claim 9, wherein the restriction endonuclease is selected from the group consisting of Mspl, HpaII, BssHIII, BstUI and NotI.

11. The method of claim 1, wherein the presence of methylated CpG-in the 5' regulatory region is indicative of a cell proliferative disorder.

12. The method of claim 11, wherein the disorder is selected from the group consisting of low grade astrocytoma, anaplastic astrocytoma, glioblastoma, medulloblastoma, colon cancer, lung cancer, renal cancer, leukemia, breast cancer, prostate cancer, endometrial cancer and neuroblastoma.

13. The method of claim 1, wherein the primers hybridize with a target polynucleotide sequence having the sequence selected from the group consisting of SEQ ID Nos: 1–24.

14. The method of claim 1, wherein the primers are selected from the group consisting of SEQ ID Nos: 25–48.

* * * * *

UNITED STATES PATENT AND TRADEMARK OFFICE
CERTIFICATE OF CORRECTION

PATENT NO.   : 6,265,171 B1  
DATED         : July 24, 2001  
INVENTOR(S)  : Herman et al.

Page 1 of 1

It is certified that error appears in the above-identified patent and that said Letters Patent is hereby corrected as shown below:

<u>Column 1,</u>
Line 15, please insert the following:
-- GOVERNMENTAL SUPPORT
This invention was made with government support under Grant Nos. CA43318 and CA54396 awarded by the National Institutes of Health. The government has certain rights in this invention. --

Signed and Sealed this

Twenty-eighth Day of May, 2002

Attest:

JAMES E. ROGAN  
*Attesting Officer*     *Director of the United States Patent and Trademark Office*

SEQUENCE LISTING (1) GENERAL INFORMATION:

(iii) NUMBER OF SEQUENCES: 216

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GCGGTCCGCC CCACCCTCTG            20

(2) INFORMATION FOR SEQ ID NO:2:

(i) SEQUENCE CHARACTERISTICS:
      (A) LENGTH:16 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

CCACGGCCGC GGCCCG            16

(2) INFORMATION FOR SEQ ID NO:3:

(i) SEQUENCE CHARACTERISTICS:
    (A) LENGTH:24 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:3:

GCGATCCGCC CCACCCTCTA ATAA                                          24

(2) INFORMATION FOR SEQ ID NO:4:

(i) SEQUENCE CHARACTERISTICS:
        (A) LENGTH:21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTACGGTCGC GGTTCGGGGT C                                             21

(2) INFORMATION FOR SEQ ID NO:5:

(i) SEQUENCE CHARACTERISTICS:
        (A) LENGTH:24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ACAATCCACC CCACCCTCTA ATAA                                          24

(2) INFORMATION FOR SEQ ID NO:6:

(i) SEQUENCE CHARACTERISTICS:
        (A) LENGTH:22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TTATGGTTGT GGTTTGGGGT TG                                            22

(2) INFORMATION FOR SEQ ID NO:7:

(i) SEQUENCE CHARACTERISTICS:
        (A) LENGTH:24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GCGATCCGCC CCACCCTCTA ATAA                                          24

(2) INFORMATION FOR SEQ ID NO:8:

(i) SEQUENCE CHARACTERISTICS:
        (A) LENGTH:23 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:8:

CGGTCGGAGG TCGATTTAGG TGG                                               23

(2) INFORMATION FOR SEQ ID NO:9:

(i) SEQUENCE CHARACTERISTICS:
        (A) LENGTH:24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ACAATCCACC CCACCCTCTA ATAA                                              24

(2) INFORMATION FOR SEQ ID NO:10:

(i) SEQUENCE CHARACTERISTICS:
        (A) LENGTH:23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

TGGTTGGAGG TTGATTTAGG TGG                                               23

(2) INFORMATION FOR SEQ ID NO:11:

(i) SEQUENCE CHARACTERISTICS:
        (A) LENGTH:17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TCTGGCCGCA GGGTGCG                                                      17

(2) INFORMATION FOR SEQ ID NO:12:

(i) SEQUENCE CHARACTERISTICS:
        (A) LENGTH:17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CCGGCCGCTC GGCCACT                                                      17

(2) INFORMATION FOR SEQ ID NO:13:

(i) SEQUENCE CHARACTERISTICS:
        (A) LENGTH:19 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:13:

AACCGCAAAA TACGAACGC                                                      19

(2) INFORMATION FOR SEQ ID NO:14:

(i) SEQUENCE CHARACTERISTICS:
        (A) LENGTH:22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TCGGTCGTTC GGTTATTGTA CG                                                  22

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

AACCACAAAA TACAAACACA TCACA                                               25

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TTGGTTGTTT GGTTATTGTA TGG                                                 23

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GCGTACGCAA AAAAATCCTC CA                                                  22

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TTCGCGGCGT TCGGTTC                                                        17

(2) INFORMATION FOR SEQ ID NO:19:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:19:

ACATACACAA AAAAATCCTC CAAC                                          24

(2) INFORMATION FOR SEQ ID NO:20:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:20:

TTTGTGGTGT TTGGTTTGGG                                               20

(2) INFORMATION FOR SEQ ID NO:21:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:21:

ACGCGATAAC CCTCTAACCT AA                                            22

(2) INFORMATION FOR SEQ ID NO:22:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:22:

GTCGGTAGGT GAATTTTTAG TTA                                           23

(2) INFORMATION FOR SEQ ID NO:23:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:23:

ACAATAACCC TCTAACCTAA AATTA                                         25

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TGTGTTGTTG ATTGGTTGTG                                           20

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GCGACCTCTA AATACCTAAA ACCC                                      24

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

CGTAGAGGTT TTATAGGTTA TTTGGA                                    26

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

ACAACCTCTA AATACCTAAA ACCC                                      24

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TGTAGAGGTT TTATAGGTTA TTTGGT                                    26

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:29:

GACGAACTTA CTACTATCCA AATACAC                                              27

(2) INFORMATION FOR SEQ ID NO:30:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:30:

TTTACGGTTA GATCGGTTTT TTTTACG                                              27

(2) INFORMATION FOR SEQ ID NO:31:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:31:

AACAAACTTA CTACTATCCA AATACACC                                             28

(2) INFORMATION FOR SEQ ID NO:32:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:32:

TGGTTAGATT GGTTTTTTTT ATGG                                                 24

(2) INFORMATION FOR SEQ ID NO:33:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:33:

GCCCCCGACT CCCGAAATAA A                                                    21

(2) INFORMATION FOR SEQ ID NO:34:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:34:

CGTCGTCGGA GTTTTTGTAC GTT                                    23

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

ACCCCCAACT CCCAAAATAA AAAA                                   24

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TGTTGTTGGA GTTTTTGTAT GTTT                                   24

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

GACGACCGCT ACACCCCGAA                                        20

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

CGTCGTGATT TTAGTATTGG GGC                                    23

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

AACAACCACT ACACCCCAAA CATC                                   24

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

TGTTGTGATT TTAGTATTGG GGTGG     25

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

GCCAACGACT ACTCTTATTC CCG     23

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

CGTCGTCGTT TTTATAGGGT TTTG     24

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

ACCAACAACT ACTCTTATTC CCACC     25

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

TGTTGTTGTT TTTATAGGGT TTTGG     25

(2) INFORMATION FOR SEQ ID NO:45:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:45:

GACGCACAAC CGACTACGAC                                          20

(2) INFORMATION FOR SEQ ID NO:46:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:46:

CGGCGTTAGG GCGGGTATC                                           19

(2) INFORMATION FOR SEQ ID NO:47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:47:

AACACACAAC CAACTACAAC CC                                       22

(2) INFORMATION FOR SEQ ID NO:48:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:48:

TGGTGTTAGG GTGGGTATTG TG                                       22

(2) INFORMATION FOR SEQ ID NO:49:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:49:

GCGTAACCAA AAAAAATAAA TAATATAC                                 28

(2) INFORMATION FOR SEQ ID NO:50:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:50:

CGCGTTGGTG AGTTATGA                                                       18

(2) INFORMATION FOR SEQ ID NO:51:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:51:

ACATAACCAA AAAAAATAAA TAATATACAA                                          30

(2) INFORMATION FOR SEQ ID NO:52:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:52:

TGTGTTGGTG AGTTATGAGT GTTAAG                                              26

(2) INFORMATION FOR SEQ ID NO:53:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:53:

GACCGCGCTA CCTTCTACGA ATAT                                                24

(2) INFORMATION FOR SEQ ID NO:54:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:54:

CGCGGGAGGG GTTCGTT                                                        17

(2) INFORMATION FOR SEQ ID NO:55:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:55:

```
AACCACACTA CCTTCTACAA ATATATTTAC TA                                     32

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

TGTGGGAGGG GTTTGTTTTG                                                    20

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

GCGACCCTAA TAAAACGTCT ACGT                                               24

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

CGCGGGTAGT TACGATGAGG                                                    20

(2) INFORMATION FOR SEQ ID NO:59:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

ACAACCCTAA TAAAACATCT ACATCAAAA                                          29

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:60:

TGTGGGTAGT TATGATGAGG TGGT                                               24
```

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:61:

GAACGACATT TTAACGCCAA AAA                                         23

(2) INFORMATION FOR SEQ ID NO:62:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

CGGCGGGGA AGTTATTTA                                               19

(2) INFORMATION FOR SEQ ID NO:63:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

AAACAACATT TTAACACCAA AAAAACC                                     27

(2) INFORMATION FOR SEQ ID NO:64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

TGGTGGGGGA AGTTATTTAG TGG                                         23

(2) INFORMATION FOR SEQ ID NO:65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

GAACGACGTC CGACCACGA                                              19

(2) INFORMATION FOR SEQ ID NO:66:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

CGGTGTAGTC GAAGGAGACG TTG                                              23

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

AAACAACATC CAACCACAAC AACC                                             24

(2) INFORMATION FOR SEQ ID NO:68:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

TGGTGTAGTT GAAGGAGATG TTGTAGTTG                                        29

(2) INFORMATION FOR SEQ ID NO:69:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

GATACCCGAA TACCCCTAAC AAC                                              23

(2) INFORMATION FOR SEQ ID NO:70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

CGTCGTTTTT ACGTTTTTTT AGGG                                             24

(2) INFORMATION FOR SEQ ID NO:71:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:71:

AATACCCAAA TACCCCTAAC AACA                                              24

(2) INFORMATION FOR SEQ ID NO:72:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:72:

TGTTGTTTTT ATGTTTTTTT AGGGGA                                            26

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:73:

GCGAACTACC AAACGAACCC A                                                 21

(2) INFORMATION FOR SEQ ID NO:74:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:74:

CGCGGCGGTT AGGGAGG                                                      17

(2) INFORMATION FOR SEQ ID NO:75:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:75:

ACAAACTACC AAACAAACCC AACC                                              24

(2) INFORMATION FOR SEQ ID NO:76:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:76:

```
TGTGGTGGTT AGGGAGGTGG G                                               21

(2) INFORMATION FOR SEQ ID NO:77:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:77:

GCGCGAAAAT ATCGTCG                                                    17

(2) INFORMATION FOR SEQ ID NO:78:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:78:

CGCGTTTCGT CGGTTT                                                     16

(2) INFORMATION FOR SEQ ID NO:79:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:79:

ACACAAAAAT ATCATCACTC CATAC                                           25

(2) INFORMATION FOR SEQ ID NO:80:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:80:

TGTGTTTTGT TGGTTTTTAG GT                                              22

(2) INFORMATION FOR SEQ ID NO:81:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:81:

GACGCTAACC GCCTACAAAC A                                               21

(2) INFORMATION FOR SEQ ID NO:82:
```

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:82:

CGGTCGTTTA GGGGTGCGT                                                19

(2) INFORMATION FOR SEQ ID NO:83:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:83:

AACACTAACC ACCTACAAAC ACCCA                                         25

(2) INFORMATION FOR SEQ ID NO:84:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:84:

TGGTTGTTTA GGGGTGTGTT ATGTT                                         25

(2) INFORMATION FOR SEQ ID NO:85:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:85:

GACTCCGCCT CTACCGC                                                  17

(2) INFORMATION FOR SEQ ID NO:86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:86:

CGGTTTTTGT TAGTTTATTT CG                                            22

(2) INFORMATION FOR SEQ ID NO:87:

(i) SEQUENCE CHARACTERISTICS:
        (A) LENGTH: 22 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:87:

AACTCCACCT CTACCACCTA AT                                              22

(2) INFORMATION FOR SEQ ID NO:88:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:88:

TGGTTTTTGT TAGTTTATTT TGG                                             23

(2) INFORMATION FOR SEQ ID NO:89:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:89:

GCGCGAAAAC GAAACCGA                                                   18

(2) INFORMATION FOR SEQ ID NO:90:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:90:

CGCGTTTCGG ATATGTTGGG                                                 20

(2) INFORMATION FOR SEQ ID NO:91:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:91:

ACACAAAAAC AAAACCAAAA CAC                                             23

(2) INFORMATION FOR SEQ ID NO:92:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:92:

TGTGTTTTGG ATATGTTGGG A                                              21

(2) INFORMATION FOR SEQ ID NO:93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:93:

GAACGTCCCT CAACGCCGTA A                                              21

(2) INFORMATION FOR SEQ ID NO:94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:94:

CGTATGCGCG GTAGGTCGTT T                                              21

(2) INFORMATION FOR SEQ ID NO:95:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:95:

AAACATCCCT CAACACCATA AAACTC                                         26

(2) INFORMATION FOR SEQ ID NO:96:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:96:

TGTATGTGTG GTAGGTTGTT TTTTTTTTT                                      29

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

GCGAAACTCA AACCCGAAAC                                                20

(2) INFORMATION FOR SEQ ID NO:98:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:98:

CGTTTATCGT GAGGATCGTT ATTAT                          25

(2) INFORMATION FOR SEQ ID NO:99:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:99:

ACAAAACTCA AACCCAAAAC CC                             22

(2) INFORMATION FOR SEQ ID NO:100:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:100:

TGTTTATTGT GAGGATTGTT ATTATGG                       27

(2) INFORMATION FOR SEQ ID NO:101:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:101:

GCTACTAAAC TACCCCAAAC CGTC                           24

(2) INFORMATION FOR SEQ ID NO:102:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:102:

CGGTCGTTAT GGCGGTGTC                                19

(2) INFORMATION FOR SEQ ID NO:103:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:103:

ACTACTAAAC TACCCCAAAC CATCC                                                25

(2) INFORMATION FOR SEQ ID NO:104:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:104:

TGGTTGTTAT GGTGGTGTTG GAG                                                  23

(2) INFORMATION FOR SEQ ID NO:105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:105:

CAGAGGGTGG GGCGGACCGC                                                      20

(2) INFORMATION FOR SEQ ID NO:106:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:106:

CGGGCCGCGG CCGTGG                                                          16

(2) INFORMATION FOR SEQ ID NO:107:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:107:

TTATTAGAGG GTGGGGCGGA TCGC                                                 24

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:108:

GACCCCGAAC CGCGACCGTA A                                              21

(2) INFORMATION FOR SEQ ID NO:109:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:109:

TTATTAGAGG GTGGGGTGGA TTGT                                           24

(2) INFORMATION FOR SEQ ID NO:110:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:110:

CAACCCCAAA CCACAACCAT AA                                             22

(2) INFORMATION FOR SEQ ID NO:111:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:111:

TACTTATTAG AGGGTGGGGC GGATCGC                                        27

(2) INFORMATION FOR SEQ ID NO:112:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:112:

CCACCTAAAT CGACCTCCGA CCG                                            23

(2) INFORMATION FOR SEQ ID NO:113:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:113:

TTATTAGAGG GTGGGGTGGA TTGT                                            24

(2) INFORMATION FOR SEQ ID NO:114:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:114:

CCACCTAAAT CAACCTCCAA CCA                                             23

(2) INFORMATION FOR SEQ ID NO:115:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:115:

CGCACCCTGC GGCCAGA                                                    17

(2) INFORMATION FOR SEQ ID NO:116:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:116:

AGTGGCCGAGC GGCCGG                                                    17

(2) INFORMATION FOR SEQ ID NO:117:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:117:

GCGTTCGTAT TTTGCGGTT                                                  19

(2) INFORMATION FOR SEQ ID NO:118:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:118:

CGTACAATAA CCGAACGACC GA                                              22

(2) INFORMATION FOR SEQ ID NO:119:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:119:

TGTGATGTGT TTGTATTTTG TGGTT                                    25

(2) INFORMATION FOR SEQ ID NO:120:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:120:

CCATACAATA ACCAAACAAC CAA                                     23

(2) INFORMATION FOR SEQ ID NO:121:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:121:

TGGAGGATTT TTTTGCGTAC GC                                      22

(2) INFORMATION FOR SEQ ID NO:122:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:122:

GAACCGAACG CCGCGAA                                            17

(2) INFORMATION FOR SEQ ID NO:123:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:123:

GTTGGAGGAT TTTTTTGTGT ATGT                                    24

(2) INFORMATION FOR SEQ ID NO:124:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:124:

CCCAAACCAA ACACCACAAA                                                    20

(2) INFORMATION FOR SEQ ID NO:125:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:125:

TTAGGTTAGA GGGTTATCGC GT                                                 22

(2) INFORMATION FOR SEQ ID NO:126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:126:

TAACTAAAAA TTCACCTACC GAC                                                23

(2) INFORMATION FOR SEQ ID NO:127:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:127:

TAATTTTAGG TTAGAGGGTT ATTGT                                              25

(2) INFORMATION FOR SEQ ID NO:128:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:128:

CACAACCAAT CAACAACACA                                                    20

(2) INFORMATION FOR SEQ ID NO:129:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:129:

GGGTTTTAGG TATTTAGAGG TCGC                                                  24

(2) INFORMATION FOR SEQ ID NO:130:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:130:

ACCAAATAAC CTATAAAACC TCTACG                                                26

(2) INFORMATION FOR SEQ ID NO:131:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:131:

GGGTTTTAGG TATTTAGAGG TTGT                                                  24

(2) INFORMATION FOR SEQ ID NO:132:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:132:

ACCAAATAAC CTATAAAACC TCTACA                                                26

(2) INFORMATION FOR SEQ ID NO:133:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:133:

GTGTATTTGG ATAGTAGTAA GTTCGTC                                               27

(2) INFORMATION FOR SEQ ID NO:134:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:134:

```
CGTAAAAAAA ACCGATCTAA CCGTAAA                                        27

(2) INFORMATION FOR SEQ ID NO:135:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:135:

GGTGTATTTG GATAGTAGTA AGTTTGTT                                       28

(2) INFORMATION FOR SEQ ID NO:136:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:136:

CCATAAAAAA AACCAATCTA ACCA                                           24

(2) INFORMATION FOR SEQ ID NO:137:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:137:

TTTATTTCGG GAGTCGGGGG C                                              21

(2) INFORMATION FOR SEQ ID NO:138:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:138:

AACGTACAAA AACTCCGACG ACG                                            23

(2) INFORMATION FOR SEQ ID NO:139:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:139:

TTTTTTATTT TGGGAGTTGG GGGT                                           24
```

(2) INFORMATION FOR SEQ ID NO:140:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:140:

AAACATACAA AAACTCCAAC AACA                                      24

(2) INFORMATION FOR SEQ ID NO:141:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:141:

TTCGGGGTGT AGCGGTCGTC                                          20

(2) INFORMATION FOR SEQ ID NO:142:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:142:

GCCCCAATAC TAAAATCACG ACG                                      23

(2) INFORMATION FOR SEQ ID NO:143:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:143:

GATGTTTGGG GTGTAGTGGT TGTT                                      24

(2) INFORMATION FOR SEQ ID NO:144:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:144:

CCACCCCAAT ACTAAAATCA CAACA                                    25

(2) INFORMATION FOR SEQ ID NO:145:

(i) SEQUENCE CHARACTERISTICS:
        (A) LENGTH: 23 base pairs (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:145:

CGGGAATAAG AGTAGTCGTT GGC                                             23

(2) INFORMATION FOR SEQ ID NO:146:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:146:

CAAAACCCTA TAAAAACGAC GACG                                            24

(2) INFORMATION FOR SEQ ID NO:147:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:147:

GGTGGGAATA AGAGTAGTTG TTGGT                                           25

(2) INFORMATION FOR SEQ ID NO:148:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:148:

CCAAAACCCT ATAAAAACAA CAACA                                           25

(2) INFORMATION FOR SEQ ID NO:149:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:149:

GTCGTAGTCG GTTGTGCGTC                                                 20

(2) INFORMATION FOR SEQ ID NO:150:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:150:

GATACCCGCC CTAACGCCG                                          19

(2) INFORMATION FOR SEQ ID NO:151:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:151:

GGGTTGTAGT TGGTTGTGTG TT                                      22

(2) INFORMATION FOR SEQ ID NO:152:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:152:

CACAATACCC ACCCTAACAC CA                                      22

(2) INFORMATION FOR SEQ ID NO:153:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:153:

GTATATTATT TATTTTTTTT GGTTACGC                                28

(2) INFORMATION FOR SEQ ID NO:154:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:154:

TCATAACTCG CCAACGCG                                           18

(2) INFORMATION FOR SEQ ID NO:155:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:155:

```
TTGTATATTA TTTATTTTTT TTGGTTATGT                                              30
```

(2) INFORMATION FOR SEQ ID NO:156:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:156:

```
CTTAACACTC ATAACTCACC AACACA                                                  26
```

(2) INFORMATION FOR SEQ ID NO:157:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:157:

```
ATATTCGTAG AAGGTAGCGC GGTC                                                    24
```

(2) INFORMATION FOR SEQ ID NO:158:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:158:

```
AACGAACCCC TCCCGCG                                                            17
```

(2) INFORMATION FOR SEQ ID NO:159:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:159:

```
TAGTAAATAT ATTTGTAGAA GGTAGTGTGG TT                                           32
```

(2) INFORMATION FOR SEQ ID NO:160:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:160:

```
CAAAACAAAC CCCTCCCACA                                                         20
```

(2) INFORMATION FOR SEQ ID NO:161:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:161:

ACGTAGACGT TTTATTAGGG TCGC                                              24

(2) INFORMATION FOR SEQ ID NO:162:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:162:

CCTCATCGTA ACTACCCGCG                                                   20

(2) INFORMATION FOR SEQ ID NO:163:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:163:

TTTTGATGTA GATGTTTTAT TAGGGTTGT                                         29

(2) INFORMATION FOR SEQ ID NO:164:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:164:

ACCACCTCAT CATAACTACC CACA                                              24

(2) INFORMATION FOR SEQ ID NO:165:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:165:

TTTTTGGCGT TAAAATGTCG TTC                                               23

(2) INFORMATION FOR SEQ ID NO:166:

(i) SEQUENCE CHARACTERISTICS:
            (A) LENGTH: 19 base pairs
            (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:166:

TAAATAACTT CCCCCGCCG                                                19

(2) INFORMATION FOR SEQ ID NO:167:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:167:

GGTTTTTTTG GTGTTAAAAT GTTGTTT                                       27

(2) INFORMATION FOR SEQ ID NO:168:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:168:

CCACTAAATA ACTTCCCCCA CCA                                           23

(2) INFORMATION FOR SEQ ID NO:169:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:169:

TCGTGGTCGG ACGTCGTTC                                                19

(2) INFORMATION FOR SEQ ID NO:170:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:170:

CAACGTCTCC TTCGACTACA CCG                                           23

(2) INFORMATION FOR SEQ ID NO:171:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:171:

GGTTGTTGTG GTTGGATGTT GTTT                                    24

(2) INFORMATION FOR SEQ ID NO:172:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:172:

CAACTACAAC ATCTCCTTCA ACTACACCA                                29

(2) INFORMATION FOR SEQ ID NO:173:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:173:

GTTGTTAGGG GTATTCGGGT ATC                                     23

(2) INFORMATION FOR SEQ ID NO:174:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:174:

CCCTAAAAAA ACGTAAAAAC GACG                                    24

(2) INFORMATION FOR SEQ ID NO:175:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:175:

TGTTGTTAGG GGTATTTGGG TATT                                    24

(2) INFORMATION FOR SEQ ID NO:176:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:176:

TCCCCTAAAA AAACATAAAA ACAACA                                  26

(2) INFORMATION FOR SEQ ID NO:177:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:177:

TGGGTTCGTT TGGTAGTTCG C                                          21

(2) INFORMATION FOR SEQ ID NO:178:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:178:

CCTCCCTAAC CGCCGCG                                               17

(2) INFORMATION FOR SEQ ID NO:179:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:179:

GGTTGGGTTT GTTTGGTAGT TTGT                                       24

(2) INFORMATION FOR SEQ ID NO:180:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:180:

CCCACCTCCC TAACCACCAC A                                          21

(2) INFORMATION FOR SEQ ID NO:181:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:181:

CGACGATATT TTCGCGC                                               17

(2) INFORMATION FOR SEQ ID NO:182:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:182:

AAACCGACGA AACGCG                                                         16

(2) INFORMATION FOR SEQ ID NO:183:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:183:

GTATGGAGTG ATGATATTTT TGTGT                                               25

(2) INFORMATION FOR SEQ ID NO:184:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:184:

ACCTAAAAAC CAACAAAACA CA                                                  22

(2) INFORMATION FOR SEQ ID NO:185:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:185:

TGTTTGTAGG CGGTTAGCGT C                                                   21

(2) INFORMATION FOR SEQ ID NO:186:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:186:

ACGCACCCCT AAACGACCG                                                      19

(2) INFORMATION FOR SEQ ID NO:187:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:187:

TGGGTGTTTG TAGGTGGTTA GTGTT                                              25

(2) INFORMATION FOR SEQ ID NO:188:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:188:

AACATAACAC ACCCCTAAAC AACCA                                              25

(2) INFORMATION FOR SEQ ID NO:189:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:189:

GCGGTAGAGG CGGAGTC                                                       17

(2) INFORMATION FOR SEQ ID NO:190:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:190:

CGAAATAAAC TAACAAAAAC CG                                                 22

(2) INFORMATION FOR SEQ ID NO:191:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:191:

ATTAGGTGGT AGAGGTGGAG TT                                                 22

(2) INFORMATION FOR SEQ ID NO:192:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:192:

CCAAAATAAA CTAACAAAAA CCA                                              23

(2) INFORMATION FOR SEQ ID NO:193:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:193:

TCGGTTTCGT TTTCGCGC                                                    18

(2) INFORMATION FOR SEQ ID NO:194:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:194:

CCCAACATAT CCGAAACGCG                                                  20

(2) INFORMATION FOR SEQ ID NO:195:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:195:

GTGTTTTGGT TTTGTTTTTG TGT                                              23

(2) INFORMATION FOR SEQ ID NO:196:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:196:

TCCCAACATA TCCAAAACAC A                                                21

(2) INFORMATION FOR SEQ ID NO:197:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:197:

TTACGGCGTT GAGGGACGTT C                                                21

(2) INFORMATION FOR SEQ ID NO:198:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:198:

AAACGACCTA CCGCGCATAC G                                        21

(2) INFORMATION FOR SEQ ID NO:199:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:199:

GAGTTTTATG GTGTTGAGGG ATGTTT                                26

(2) INFORMATION FOR SEQ ID NO:200:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:200:

AAAAAAAAAA ACAACCTACC ACACATACA                           29

(2) INFORMATION FOR SEQ ID NO:201:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:201:

GTTTCGGGTT TGAGTTTCGC                                          20

(2) INFORMATION FOR SEQ ID NO:202:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:202:

ATAATAACGA TCCTCACGAT AAACG                                  25

(2) INFORMATION FOR SEQ ID NO:203:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:203:

GGGTTTTGGG TTTGAGTTTT GT                                                22

(2) INFORMATION FOR SEQ ID NO:204:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:204:

CCATAATAAC AATCCTCACA ATAAACA                                           27

(2) INFORMATION FOR SEQ ID NO:205:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:205:

GACGGTTTGG GGTAGTTTAG TAGC                                              24

(2) INFORMATION FOR SEQ ID NO:206:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:206:

GACACCGCCA TAACGACCG                                                    19

(2) INFORMATION FOR SEQ ID NO:207:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:207:

GGATGGTTTG GGGTAGTTTA GTAGT                                             25

(2) INFORMATION FOR SEQ ID NO:208:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:208:

CTCCAACACC ACCATAACAA CCA                                          23

(2) INFORMATION FOR SEQ ID NO:209:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:209:

TTTTTAGAGG ATTTGAGGGA TAGG                                         24

(2) INFORMATION FOR SEQ ID NO:210:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:210:

CTACCTAATT CCAATTCCCC TACA                                         24

(2) INFORMATION FOR SEQ ID NO:211:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:211:

GTTTTCCCAG TCACGACAGT ATTAGGAGGA AGAAAGAGGA G                       41

(2) INFORMATION FOR SEQ ID NO:212:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:212:

TCCAATTCCC CTACAAACTT C                                            21

(2) INFORMATION FOR SEQ ID NO:213:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:213:

```
                                          -continued

CTACCTAATT CCAATTCCCC TACA                                              24

(2) INFORMATION FOR SEQ ID NO:214:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:214:

TCATTAGAGG GTGGGGCGGA TCGC                                              24

(2) INFORMATION FOR SEQ ID NO:215:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:215:

CCTTATTAGA GGGTGGGGCG GATCGC                                            26

(2) INFORMATION FOR SEQ ID NO:216:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:216:

TGGCAACCCC AAACCACAAC CATAA                                             25
```